US006446509B1

United States Patent
Takada et al.

(12) United States Patent
Takada et al.

(10) Patent No.: US 6,446,509 B1
(45) Date of Patent: Sep. 10, 2002

(54) METHOD AND APPARATUS FOR ULTRASONIC TESTING OF THE SURFACE OF COLUMNAR STRUCTURES, AND METHOD FOR GRINDING ROLLS BY USE OF THEM

(75) Inventors: Hajime Takada; Ryouichi Sugimoto; Takashi Morii; Ikuo Yarita, all of Chiba (JP)

(73) Assignee: Kawasaki Steel Corporation, Hyogo (JP)

( * ) Notice: Subject to any disclaimer, the term of this patent is extended or adjusted under 35 U.S.C. 154(b) by 0 days.

(21) Appl. No.: 09/319,979

(22) PCT Filed: Oct. 29, 1998

(86) PCT No.: PCT/JP98/04897

§ 371 (c)(1),
(2), (4) Date: Jun. 15, 1999

(87) PCT Pub. No.: WO99/23486

PCT Pub. Date: May 14, 1999

(30) Foreign Application Priority Data

| Oct. 31, 1997 | (JP) | 9-300409 |
| Dec. 1, 1997 | (JP) | 9-330213 |
| May 12, 1998 | (JP) | 10-128912 |

(51) Int. Cl.$^7$ ............................................. G01N 29/04
(52) U.S. Cl. ............................ 73/627; 73/593; 73/598; 73/600; 73/602; 73/620
(58) Field of Search ........................ 73/570, 622, 620, 73/627, 629, 593, 600, 602, 637, 632; 367/140, 155, 167, 164; 310/311, 325, 359

(56) References Cited

U.S. PATENT DOCUMENTS

| 4,307,614 A | 12/1981 | Tittmann et al. | 73/629 |
| 4,338,822 A * | 7/1982 | Yamaguchi et al. | 73/643 |
| 4,406,167 A * | 9/1983 | Maeda | 73/622 |
| 4,651,310 A * | 3/1987 | Kaneko et al. | 367/140 |
| 4,725,994 A * | 2/1988 | Kaneko et al. | 367/140 |
| 5,005,417 A * | 4/1991 | Kawasaki et al. | 73/593 |
| 5,056,368 A * | 10/1991 | Kawasaki et al. | 73/642 |
| 5,469,743 A * | 11/1995 | Zorn | 73/627 |
| 6,065,343 A * | 5/2000 | Kiuchi et al. | 73/622 |
| 6,105,408 A * | 8/2000 | Scharlemann | 72/31.07 |

FOREIGN PATENT DOCUMENTS

| JP | A-60-232858 | 11/1985 |
| JP | A-63-255657 | 10/1988 |
| JP | A-2-73151 | 3/1990 |
| JP | A-4-276547 | 10/1992 |
| JP | A-7-294493 | 11/1995 |

* cited by examiner

Primary Examiner—Hezron Williamd
Assistant Examiner—Jacques Saint-Surin
(74) Attorney, Agent, or Firm—Oliff & Berridge, PLC

(57) ABSTRACT

An ultrasonic testing method uses surface waves to prevent false detection of primary cracks, to lower the level of structural noises from grain boundaries, and to improve the detectability in the ultrasonic testing by surface wave testing of hot rolling rolls. A surface wave probe 10 capable of transmitting and receiving a surface wave is provided with a piezoelectric element 10A, a resin wedge 10C disposed on the front surface of the piezoelectric element 10A and a damping block 10B disposed on the back surface. The surface wave probe 10 is driven to produce a short pulse having a pulse length being at most 2.5 times the wavelength of the surface wave to be produced. A coupling liquid medium is supplied to the probe 10 in accordance with the peripheral speed of the roll to be tested. Depending on the height of the reflected waves measured, the grinding allowance of the roll is determined, and the roll is ground according to the thus-determined grinding allowance. The roll may be tested while being partly ground, and the optimum grinding allowance of the roll may be determined.

11 Claims, 18 Drawing Sheets

METHOD AND APPARATUS FOR ULTRASONIC TESTING OF THE SURFACE OF COLUMNAR STRUCTURES, AND METHOD FOR GRINDING ROLLS BY USE OF THEM

TECHNICAL FIELD

The present invention relates to a method and an apparatus for ultrasonic testing of the surface of columnar structures of metal, such as rolls for rolling mills, rollers and others, especially to those suitable for detecting, using surface waves, flaws such as cracks or the like existing in and just below the surface of high-speed tool steel rolls for hot rolling mills, which are made of high-speed tool steel and of which the surface is thermally/mechanically damaged while they are used for rolling, and also to a method for grinding rolls using them.

BACKGROUND OF THE INVENTION

Rolls for hot rolling of metal sheets are thermally/mechanically damaged at their surface while they are used for rolling. The details of thermal/mechanical damage at the surface of a work roll (hereinafter referred to as a high-speed tool steel roll for former stands in finishing train), which is made of high-speed tool steel and is used in hot finish rolling, are described with reference to FIG. 20. Thermal damage to the roll is caused by steel sheets being rolled at high temperatures in former stands in finishing train, whereby deep primary cracks K, which are referred to as fire cracks, are formed in the roll 100 vertically to its surface. Mechanical damage thereto is caused by the shear stress to be put on the roll being rolled against backup rolls, whereby are formed secondary cracks L starting from the above-mentioned fire cracks K in the direction nearly in parallel with the surface of the roll. A plurality of those cracks gathers to give small pits M on the surface of the roll. If such small pits M are transferred onto the sheets being rolled, the rolled sheets shall have surface flaws. In order to evade this, the cracks are removed from rolls, for example, by means of grinding by a predetermined constant grinding allowance with a grinder, and the thus-ground rolls are again used in rolling. After having been ground, the rolls are tested by surface wave technique (hereinafter referred to as surface wave testing), for example, as in JP-A-4-276547.

Concretely, a surface wave probe (search unit) is kept in contact with the surface of a rotating roll via a membrane of a coupling liquid medium such as water or the like, whereby the surface waves from said surface wave probe is propagated inside the circumferential surface of the roll toward the direction opposite to the direction in which the roll is rotating while the liquid having been used as coupling medium is removed from the path of the surface waves in the surface of the roll. In that manner, the flaws, if any, existing in and just below the surface of the roll are detected. If some flaws are detected in such surface wave testing of rolls, the rolls shall be again ground.

An ultrasonic test apparatus is disclosed in JP-A-7-294493, to which is applied the testing method of JP-A-4-276547. The ultrasonic test apparatus comprises a rotating means for rotating a cylindrical or columnar structure to be tested for surface flaws and others, in its circumferential direction; an ultrasonic probe for detecting flaws and others by use of surface waves; a holder for holding the probe above the structure to be tested at a predetermined height relative to the surface of the structure; and a couplant supply for supplying a liquid medium such as water or the like to be a coupling medium for ultrasound transmission, to the gap between the probe and the structure to be tested. The above-mentioned holder extends downward below the probe, and has a following part to be in smooth contact with the surface of the structure to be tested. While kept in contact with the rotating structure to be tested, the following part ensures the constant distance between the probe and the structure. The above-mentioned couplant supply is disposed adjacent to the probe inside the holder. The couplant supply is provided with a housing in which the liquid medium having been led near the probe from the other place is stored. The housing is positioned adjacent to the probe, and has a lot of medium outlets at its bottom and an air-discharging through-hole at its top. Each of the medium outlets is placed just in front of the probe relative to the scanning direction of probe, while the surface of the structure being rotated to be tested is scanned by the probe, and is so disposed that it intersects the above-mentioned circumferential direction. In that constitution, the liquid medium stored in the housing is fed through those medium outlets to the gap between the probe and the surface of the structure being tested, at the place just in front of the leading edge of the probe.

Recently, however, it has been clarified that, when the testing method according to JP-A-4-276547 is applied to the detection of flaws existing in and just below the surface of high-speed tool steel rolls, especially those for former stands in finishing train, there occur serious problems such as those mentioned below.

Specifically, the small pits M shown in FIG. 20 are not formed in the absence of the secondary cracks L. Therefore, in order to prevent the formation of the small pits M, only the secondary cracks L are to be removed through grinding. However, according to the conventional ultrasonic testing method, often observed is the phenomenon of large-amplitude reflected waves appearing even after all those secondary cracks L are removed. Grinding rolls until no such reflected wave appears results in the thorough removal of the primary cracks K needless to be removed, whereby the roll consumption shall increase.

This is because, in the surface wave testing, the reflectivity of the flaws vertical to the surface of the roll being tested is high. In this, therefore, the primary cracks K remain are detected falsely even after all the secondary cracks L are removed. The depth of the primary cracks K remain is considerably shallow, the amplitude of the wave reflected on each primary crack K remains is very small. However, in the surface of the roll, there are innumerable primary cracks K remain, and there are also innumerable reflectors by which the surface waves are reflected. Where a structure (herein roll) having such innumerable small reflectors is tested by surface waves having a wavelength of $\lambda$, there always exist combinations of small reflectors between which the difference in the distance from the surface wave probe 10 is $\lambda/2$, as shown in FIG. 21. FIG. 21 shows examples of the combinations of such small reflectors, in which small reflectors K1 to K4 correspond to the combinations.

Where the region in which the small reflectors K1 to K4 exist is tested in a conventional manner using a narrow bandwidth pulse of which the length is at least 5 times larger than the wavelength of the resulting surface wave, small reflected waves from those reflectors overlap in phase with each other, owing to the large pulse length, thereby enlarging their amplitude to give a large reflected wave that may indicate the presence of just like a large flaw, as shown in FIG. 22. Specifically, since such a narrow bandwidth pulse of which the length is at least 5 times larger than the wavelength of the resulting surface wave is used in surface wave testing of high-speed tool steel rolls for former stands in finishing train, the amplitude of the reflected waves from the primary cracks K is detected too high in the test. As a result, the rolls are to be ground until the amplitude of the reflected waves from the primary cracks, K becomes lower than a predetermined voltage. Consequently, since the primary cracks K are almost completely removed, or that is, since the rolls are too much ground, the roll consumption is to increase.

In this connection, it may be taken into consideration to elevate the threshold voltage that is settled for detecting flaws to a degree not bringing about false detection of the primary cracks K. However, elevating the threshold voltage lowers the detectabilities of the test device, and therefore, there is a danger of overlooking cracks and the like which exist alone (these are produced by rolling accidents) and which must be detected.

The problems with the ultrasonic testing mentioned above are not related to only the primary cracks of rolls for rolling mills but also others. Where ordinary columnar structures of metal such as rollers and the like having a coarse grained structure and producing scattered waves at their grain boundaries are tested, using the conventional narrow bandwidth pulse, formed are high structural noises owing to the same mechanisms as those of the phenomenon previously mentioned hereinabove. Therefore, there are the same problems as above with the ultrasonic testing of that type.

On the other hand, the layer thickness of the thermal/mechanical damaged zone generated inside the rolls having been used in rolling greatly varies, depending on the length of the metal sheet rolled by the use of the rolls, the rolling speed, the condition for cooling the rolls, the material of the rolls (even rolls of the same type often differ in the details of the material owing to the difference in the manufacture method for the material), etc. Therefore, where the rolls are ground by a predetermined constant grinding allowance, there occur the problems mentioned below.

① Where the thermal/mechanical load imparted to the rolls is small and the layer thickness of the thermal/mechanical damaged zone generated inside them is thin, the rolls are ground to remove even the part not damaged (overgrinding), or that is, the rolls are too much ground, whereby the roll consumption increases.

② Where the thermal/mechanical load imparted to the rolls is large and the layer thickness of the thermal/mechanical damaged zone generated inside them is thick, the damaged zone still remains even after the rolls are ground by a predetermined constant grinding allowance. When the thus-ground rolls are tested, some false indications occur. In that case, the rolls will have to be further ground. However, since the layer thickness of the remaining thermal/mechanical damaged zone is not clarified, the grinding allowance of the additional grinding must be the same as that of the initial grinding. In most cases, therefore, the rolls are too much ground (overground), or that is, the degree of the total grinding is too large, whereby the roll consumption increases.

③ The overall time taken for grinding the rolls is prolonged by the time taken for the over grinding, and the roll grinding efficiency is lowered.

In the ultrasonic test apparatus disclosed in JP-A-7-294493, nothing is taken into consideration relative to the relationship between the rotating speed of the structure to be tested and the necessary amount of the coupling liquid medium. However, depending on the rotating speed of the structure to be tested, the amount of the coupling liquid medium that is trained by the rotating surface of the structure being tested varies. For example, with the increase in the rotating speed of the structure being tested, the amount of the coupling liquid medium that is taken out of the gap between the probe and the surface of the structure increases, thereby resulting in that the amount of the coupling liquid medium to be in the gap between the probe and the surface of the structure is short. As a result, ultrasonic waves could not be well transmitted into the structure to be tested, and some surface flaws of the structure could not be detected. On the contrary, when the rotating speed of the roll is slow, the surplus coupling liquid medium flows out ahead of the probe, thereby attenuating surface waves. In that case, some surface flaws of the structure could not be detected.

No concrete disclosure is given in JP-A-4-276547 and JP-A-7-294493, relating to the surface wave probe used therein, and therefore the details of the probe are unknown. However, it may be considered that a conventional known surface wave probe would be used therein. One conventional surface wave probe comprises a piezoelectric element, and a wedge via which an ultrasonic wave is introduced into the roll surface at an angle of θi, in which the incident angle θi is defined to satisfy the following formula (1) according to the laws of refraction.

$$\theta i = \sin^{-1}(CW/CRs) \quad (1)$$

wherein CW indicates the velocity of the ultrasonic wave in the wedge, and
CRs indicates the velocity of the surface wave traveling in ordinary steel.

The incident angle θi is an angle to the plane vertical to the roll surface.

Recently, however, it has been found that the flaw echoes could not have a satisfactory signal-to-noise ratio in the surface testing using the above-mentioned surface wave probe.

Accordingly, having noted the difference in the material of high-speed tool rolls owing to the difference in the production method for the material, we, the present inventors have investigated how or in what manner the difference in the material may influence the surface wave testing of the rolls. As a result, we have found that the surface wave velocity on rolls of different materials greatly differs depending on the production method, as in Table 1.

The inventors have further found that the surface wave velocity on high-speed tool steel rolls significantly differs from that on ordinary steel of being 2980 m/sec.

Transmission and receipt of surface waves in the surface of a roll by a surface wave probe is effected according to the refraction phenomenon expressed in the above-mentioned formula (1), while the incident angle θi is so defined that the angle of refraction is to be 90 degrees. Therefore, when the velocity of the surface waves varies depending on the roll materials, as in Table 1, the incident angle must be varied in accordance with the varying velocity of the surface waves. If not, transmission/receipt efficiency of the surface waves will lower.

At present, however, the incident angle θi is determined on the basis of the surface wave velocity on ordinary steel of being 2980 m/sec, and surface wave probes are designed in accordance with the thus-determined incident angle. In fact, as shown in Table 1, the surface wave velocity on different high-speed tool steel rolls significantly differs from that on ordinary steel. In addition, there are differences in the surface wave velocity between different high-speed tool rolls owing to the difference in the production method for the rolls, but, in fact, the differences in the surface wave velocity are not taken into consideration at all in designing the incident angle θi. As a result, the incident angle θi greatly differs from the optimum angle for transmission and receipt of the surface waves.

Ultrasonic testing of high-speed tool steel rolls is generally carried out at or around a roll grinding equipment. In many cases, the mechanical equipment often generates great electric noises from motors, inventors, etc., and the great electric noises are often superimposed on signals of surface wave testing. In that case, since transmission/receipt efficiency of the surface waves is really lowered in the surface wave testing for high-speed tool steel rolls, as so mentioned hereinabove, the height of the reflected waves from the flaws is lowered, thereby resulting in that the signal-to-noise ratio, echo-amplitude/electric-noises-amplitude is lowered. As a result, the detectabilities of the surface wave testing are lowered.

Even when the incident angle θi is determined in accordance with the surface wave velocity on a high-speed tool steel roll of a specific material and a surface wave probe is manufactured on the basis of the thus-determined incident angle, and when the surface wave velocity is defined to be equal to, for example, any of the smallest or largest value of 3090 m/sec or 3180 m/sec in Table 1, transmission/receipt efficiency of the surface waves for the high-speed tool steel roll having a largest or smallest surface wave velocity oppositely to the defined value is still lowered, and, in that case, the detectability in the testing are lowered. Thus, this could not still solve the problem.

Every time exchanging the surface wave probe to the best one for each roll of a different material requires a prolonged time for testing, thereby probably causing time loss in actual operation, and such is impracticable.

The present invention has been made so as to solve the problems in the conventional art noted above, and its first subject matter is to provide a method and an apparatus for ultrasonic testing of columnar structures using surface waves, in which false detection of primary cracks is prevented and the level of structural noises from grain boundaries is reduced, and of which the detectabilities are enhanced.

The second subject matter of the invention is to provide an ultrasonic test apparatus in which a suitable amount of a coupling liquid medium is always supplied to the gap between a probe and the surface of a structure to be tested even when the rotating speed of the structure is varied, thereby maintaining good transmission of ultrasonic waves to the structure and preventing any surplus coupling liquid medium from flowing out ahead of the probe.

The third subject matter of the invention is to provide a method for grinding a roll having been thermally/mechanically damaged on its surface in use for rolling or the like, in which the grinding allowance of the roll is optimized to reduce the roll consumption and to improve the roll grinding efficiency.

The fourth subject matter of the invention is to provide a method for ultrasonic testing of high-speed tool steel rolls using surface waves, in which is used a surface wave probe for roll testing capable of ensuring efficient transmission and receipt of surface waves in the rolls and capable of increasing the signal-to-noise ratio of the reflected waves from the flaws, even when the materials of the rolls differ owing to the difference in the production method, and in which the incident angle for the probe is specifically defined.

DISCLOSURE OF THE INVENTION

The invention is a method for ultrasonic testing of columnar structures, in which a surface wave probe is contacted with the surface of a rotating columnar structure via a coupling liquid medium existing therebetween, and a surface wave is propagated into the columnar structure from the surface wave probe while the probe receives the reflected waves from the flaws existing in and just below the surface of the columnar structure so as to detect the flaws. In, the method, where the center frequency of the surface wave, to be transmitted and received by the surface wave probe is fc in the frequency spectrum, the frequency bandwidth within which the spectrum magnitude falls the range between the peak value and the peak value−6 dB covers at least 0.50 fc or larger. The method of the invention has attained the above-mentioned first subject matter.

In the ultrasonic testing method of the invention to attain the above-mentioned first subject matter, the pulse length of the surface wave pulse which the surface wave probe transmits and receives is at most 2.5 times the wavelength. of the surface wave that propagates on the columnar structure.

The invention is also an apparatus for ultrasonic testing of columnar structures, in which a surface wave probe is contacted with the surface of a rotating columnar structure via a coupling liquid medium existing therebetween, and surface waves are propagated into the columnar structure from the surface wave probe while the probe receives the reflected waves from the flaws existing in and just below the surface of the columnar structure so as to detect the flaws. In the apparatus, the surface wave probe that transmits and receives the surface wave is provided with a wedge as disposed on the front surface of the piezoelectric element of the probe and with a damping block as disposed on the back surface of the piezoelectric element. The apparatus of the invention has attained the above-mentioned first subject matter.

In the invention, the piezoelectric element material is any of a lead meta-niobate, a lead titanate, a 1-3 type piezocomposite material (this is composed of rods of lead zirconate titanate (hereinafter refferred to as PZT) set in an epoxy resin matrix), a 0-3 type piezocomposite material (this is a piezoelectric material having piezoelectric ceramic grains as uniformly dispersed in polymer matrix), or a 3-1 type piezocomposite material (this is a piezoelectric material as prepared by forming a large number of through-holes in a plate of lead zirconate titanate (PZT) followed by casting an epoxy resin or the like into those through-holes and solidifying it therein).

In the invention, the wedge is made of a polyimide resin, a polystyrol resin, an acrylic resin, or a fluorine resin (Teflon).

As shown in FIG. 1, the surface wave probe 10 of the invention is essentially composed of a piezoelectric element 10A, a damping block 10B and a resin wedge 10c. When the center frequency of the surface wave which the surface wave probe 10 transmits and receives is represented by fc, then the frequency bandwidth for the probe 10 is defined to be at least 0.50 fc or larger.

Specifically, when the frequency spectrum of the surface wave which the surface wave probe 10 transmits and receives is to have a frequency distribution as conceptually shown in FIG. 2, the frequency bandwidth within which the spectrum magnitude (signal magnitude) falls the range between the peak value and the peak value−6 dB and which is represented by (fR−fL) is defined to satisfy the following formula (2):

$$fR-fL \geq 0.50 \text{ fc} \tag{2}$$

In the invention, as above, the frequency bandwidth for the surface wave probe 10 is broad and is equal to or larger than 0.50 fc. The concrete, constitution of the surface wave probe 10 is described. As the piezoelectric element 10A, usable are any piezoelectric material having a low mechanical Q value such as lead meta-niobate, piezocomposite material illustrated in FIGS. 23 to 25, etc., or any other piezoelectric material capable of being mechanically damped with ease even though having a high mechanical Q value, such as lead titanate, etc. The mechanical Q value as referred to herein is meant to indicate the sharpness of the resonance. Piezoelectric elements having a larger mechanical Q value vibrate for a longerduration when they are driven by electric pulse. The center frequency fc of the surface wave to be transmitted and received by the probe must be chosen depending on the grain size and the surface roughness of the material to be tested. For example, for rolls for rolling mills, the center frequency fc preferably is, chosen between 1 and 4 MHz.

The damping block 10B is made of a solid substance to be prepared by mixing a fine powder having a large specific gravity, such as metallic tungsten or the like, with an epoxy resin or the like followed by solidifying the resulting mixture. The damping block 10B is attached to the back surface of the piezoelectric element 10A, by which the deformation of the piezoelectric element 10A is damped. The damping block having a larger volume fraction of the heavy powder such as metallic tungsten or the like is to have a larger weight, and its damping effect on the piezoelectric element is greater, thereby resulting in that the length of the ultrasonic pulse from the probe is shortened.

The piezoelectric element 10A and the damping block 10B are so constructed as to have the material constitution defined as above, and the probe comprising them can produce (transmit) an ultrasonic pulse of which the frequency bandwidth is at least 0.5 fc or larger and the pulse length is at most 2.5 times the wavelength of the surface wave to be produced.

The resin wedge 10C is attached to the front surface of the piezoelectric element 10A in such a manner that the ultrasonic wave from the piezoelectric element can be introduced into the structure to be tested, while satisfying the following formula (3). Concretely, as shown in FIG. 1, the surface of the wedge 10C at which the piezoelectric element 10A is attached thereto is so inclined that the normal line S2 relative to the front surface of the piezoelectric element 10A intersects the normal line S1 relative to the bottom surface of the wedge 10C that is to be contacted with the surface of the structure to be tested via the coupling medium, at an incident angle θi between the two lines S1 and S2, and the front surface of the piezoelectric element 10A is attached to the inclined surface of the wedge 10C. In order to keep the short pulse waveform mentioned above, the wedge 10C itself is designed to have an attenuation coefficient as small as possible, for example, it may be made of a polystyrol resin, a polyimide resin or the like.

$$\theta i = \sin^{-1}(CW/CR) \quad (3)$$

wherein CW indicates the velocity of the ultrasonic wave in the resin wedge, and
CR indicates the velocity of the surface wave traveling in the columnar structure to be tested.

Different surface wave probes 10 having a center frequency fc=2 MHz were prepared, for which the frequency bandwidth was varied by changing the material of the damping block, and checked for the relationship between the pulse length and the frequency bandwidth. The data obtained are shown in FIG. 3, in which the frequency bandwidth equal to the center frequency fc is designated as 100%.

From FIG. 3, it is known that the probes having a frequency bandwidth of at least 50% or larger can produce short pulses of which the pulse length is at most 2.5 times the wavelength of the surface wave to be produced. The surface wave pulse thus produced to have a short pulse length is applied to flaw detection of rolls having innumerable remaining primary cracks K. Also in that case, combinations of small reflectors K1 to K4 between that the difference in the distance from the surface wave probe 10 is λ/2, λ indicating the wavelength of the surface wave traveling in the structure being tested, always exist in the structure, as in the case described hereinabove with reference to FIG. 21.

FIG. 4 shows the waveforms as observed in ultrasonic testing of a structure, in which was used a short ultrasonic pulse having a frequency bandwidth of not smaller than 0.70 fc and a pulse length of being 1.5-times the wavelength of the surface wave traveling in the structure, for testing the regions having therein small reflectors such as those mentioned above, and this corresponds to the above-mentioned FIG. 22 showing the waveforms observed in conventional ultrasonic testing.

As shown in FIG. 4, it is known that the reflected waves from the remaining primary cracks K have a small amplitude since the pulse length applied is short, and that even though those reflected waves overlap in phase with each other, the increase in the amplitude of the wave to be observed is small. Accordingly, when the surface wave probe 10 of the invention, which is so designed that it can transmit and receive a surface wave pulse having a short pulse length, is applied to flaw detection of rolls having innumerable remaining primary cracks K, the increase in the amplitude of the reflected waves from the remaining primary cracks K is effectively prevented.

The surface wave probes having a center frequency of 2 MHz but having a varying frequency bandwidth (or having a varying pulse length) were tested for the relationship between the height of the reflected waves from the primary cracks K in a work roll for former stands in finishing train, and the ratio of (pulse length/wavelength of surface wave), and the data obtained are shown in FIG. 5. In this test, the height of the reflected waves was represented with reference to the height of the reflected wave from a drilled hole that had been drilled toward the radial direction to have a diameter of 1 mm and a depth of 1 mm, and the depth of the primary cracks K was about 0.15 mm.

In the drawing, the measured points A1, A2 and A3 are for the invention, for which the piezoelectric element 10A of the surface wave probe 10 used was of a lead meta-niobate, and the damping block 10B of the probe 10 was made of a mixture of an epoxy resin with a metallic tungsten powder having a volume fraction of 80%, 60% or 40%, respectively. B1 and B2 are for comparative examples, for which the piezoelectric element 10A used was of PZT, and the damping block 10B was made of a mixture of an epoxy resin with a metallic. tungsten powder having a volume fraction of 80% or 60%, respectively. C1 and C2 are for conventional examples, for which the piezoelectric element 10A used was of PZT of two types that differ in the mechanical Q value in some degree, and the damping block 10B was not used. Except the matters specifically mentioned herein, substantially the same apparatus was used for the measurement.

From FIG. 5, it is known that the shorter pulse lengths gave reflected waves having a more lowered height from the primary cracks K.

Next, materials suitable to the piezoelectric element 10A and those suitable to the resin wedge 10C were investigated in detail. As the damping block 10B, used, was a solid mixture of an epoxy resin and a metallic tungsten powder, as in the above. In the mixture, the volume fraction of the metallic tungsten powder to be mixed with the epoxy resin was 80%, 60%, 40% or 20%. For the piezoelectric element 10A, selected were a lead meta-niobate, a lead titanate, lead zirconate titanate (PZT), barium ti-tanate, lithium niobate, a 1-3 type piezocomposite material (FIG. 23), a 0-3 type piezocomposite material (FIG. 25), and a 3-1 type piezocomposite material (FIG. 24); and for the resin wedge 10C, selected were a polyimide resin, a polystyrol resin, an acrylic resin, and a fluorine resin (Teflon) Different surface wave probes were produced in that manner, and tested to measure the frequency bandwidth and the pulse length of the surface wave to be transmitted and received by them. In addition, in the same manner as in the test for the data shown in FIG. 5, those surface wave probes were further tested to measure the height of the reflected waves from the primary cracks K in the same work roll for former stands in finishing train as that used in the test for the data in FIG. 5. For this, the height of the reflected waves was represented with reference to the height of the reflected wave from a drilled hole that had been drilled toward the radial direction to have a diameter of 1 mm and a depth of 1 mm, just in the same manner as in the test for the data in FIG. 5. The data obtained in the test in which the damping block 10B used had a volume fraction of the metallic tungsten powder of 80% are shown in Table 2; those in which the damping block 10B used had a volume fraction of the metallic tungsten powder of 60% are shown in Table 3; and those in which the damping block 10B used had a volume fraction of the metallic tungsten powder of 40% are shown in Table 4. In those Tables, the data of the probes with which the reflected waves from the primary cracks K had a height of larger than −11 dB (that is, the height of the reflected waves from the primary cracks K as seen by the use of the probes was not lower by at least 3 dB than that as seen by the use of conventional probes) were omitted, except those of the probes having a PZT. The data of the probes having a PZT are in those Tables as comparative data. Table 5 shows the data obtained in the test in which the damping block 10B used had a volume fraction of the metallic tungsten powder of 20%. As shown in Table 5, the height of the reflected waves from the primary cracks K was higher than −11 dB. Referring back to Tables 2 to 4, it is understood that, in all cases, the lead meta-niobate, the lead titanate, the 1-3 type piezocomposite material, the 0-3 type piezocomposite material and the 3-1 type piezocomposite material are all usable as the piezocomposite material 10A. It is also understood therefrom that the polyimide resin (having an attenuation coefficient at 2 MHz of $1.2 \times 10^2$ dB/m), the polystyrol resin (having an attenuation coefficient at 2 MHz of $1.3 \times 10^2$ dB/m), the acrylic resin (having an attenuation coefficient at 2 MHz of $1.8 \times 10^2$ dB/m), and the fluorine resin (Teflon, having an attenuation coefficient at 2 MHz of $1.8 \times 10^2$ dB/m) are all usable as the resin wedge 10B. Accordingly, it is known that the wedge member may have an attenuation coefficient at 2 MHz of not larger than $1.8 \times 10^2$ dB/m. Comparing the data in Tables 2 to 4 with those in Table 5, it is understood that the volume fraction of the metallic tungsten powder to be in the damping block 10B must be at least 40% or larger.

Using a conventional surface wave probe, of which the pulse length is 5 times the wavelength of the surface wave to be produced, in a substantially same condition, we, the present inventors carried out an experiment of ultrasonic testing of work rolls for former stands in finishing train. Through that our experiment, we confirmed that the height of the reflected waves from the primary cracks as seen in the testing just before the final roll grinding process was higher by 3 dB than that as seen in the testing after the final roll grinding process. Accordingly, it is believed that, if the height of the reflected waves from the primary cracks K seen in the ultrasonic testing be reduced by at least 3 dB, the number of the roll grinding repetitions could be reduced by at least one time. In this connection, the roll grinding can be finished when the height of reflected waves from the primary cracks on the ground roll are equal to or lower than predetermined threshold voltage.

Accordingly, as shown in FIG. 5, when the pulse length of the surface wave probe, with which the data of the height of the reflected waves from the primary cracks measured is lower by at least 3 dB than the data C1 as measured with the conventional surface wave probe whose pulse length is 5 times the wavelength of the surface wave to be produced, is at most 2.5 times the wavelength of the surface wave to be produced, then the difference between the measured data A3 and C1 is 3 dB. In that case, therefore, the number of the roll grinding repetitions could be reduced by at least one time.

Again referring back to FIG. 3, it may be said that the bandwidth of the surface wave probe capable of transmitting and receiving surface waves of which the pulse length is at most 2.5 times the wavelength of the surface wave to be produced is suitably 50% or larger. Accordingly, it is understood that defining the frequency bandwidth for the surface wave probe to be 0.50 fc or larger is effective for reducing any overgrinding of rolls to be caused by false detection of primary cracks of the rolls. This is the ground for defining the frequency bandwidth for the surface wave probe to be 0.50 fc or larger in the invention.

As has been described in detail hereinabove, a specific surface probe is used in the invention, for which the frequency bandwidth is defined to be 0.50 fc or larger and the pulse length is to be at most 2.5 times the wavelength of the surface wave to be produced. Comparing the data as measured by the use of the conventional surface wave probe of which the pulse length is about 5 times the wavelength of the surface wave to be produced (in FIG. 5, C1 point), and those as measured by the use of the specific surface wave probe of the invention (in FIG. 5, A1 to A3 points), it is known that the height of the reflected waves from primary cracks K as measured by the use of the specific surface wave probe of the invention is lower by from 3 to 6 dB than that as measured by the use of the conventional surface wave probe.

In the same manner as above, we, the inventors further carried out an experiment for detecting cracks having a depth of 0.5 mm in rolls in which primary cracks K having a depth of about 0.10 mm remain and those in high-speed tool steel rolls in which primary cracks K having a depth of about 0.25 mm remain. Through that our experiment, we found that the S/N ratio of the reflected waves from the cracks as measured by the use of a surface wave probe of which the pulse length was 1.5 times the wavelength of the surface wave produced was 10 dB and the S/N ratio of the reflected waves from the cracks as measured by the use of a surface wave probe of which the pulse length was 2.5 times the wavelength of surface wave produced was 7 dB, while, on the other hand, the S/N ratio of the reflected waves from the cracks as measured by the use of a conventional surface wave probe of which the pulse length was about 5 times the wavelength of the surface wave produced was about 4 dB. By use of the method of the invention, therefore, the signal-to-noise ratio of the reflected waves from cracks could be higher by about 3 to 6 dB than that by use of the conventional method, and the detectability in the invention are significantly enhanced.

Next, using an ultrasonic testing apparatus equipped with the surface wave probe 10 illustrated in FIG. 1, in which the piezoelectric element 10A, the damping block 10B and the resin wedge 10C are made of a lead meta-niobate, a mixture of an epoxy resin with a metallic tungsten powder having a volume fraction of 60%, and a polyimide resin, respectively. We, the inventors further carried out an experiment of inspecting 500 work rolls for former stands in finishing train. Specifically, in the experiment, we measured the decrement in diameter of each roll until the height of the reflected waves from the primary cracks (fire cracks) in each roll reached a predetermined level or lower. Using another ultrasonic test apparatus equipped with a conventional surface wave probe of which the pulse length is about 5 times the wavelength of the surface wave to be produced, we carried out the same experiment. As a result, the decrement in diameter of rolls by grinding by use of the apparatus equipped with the conventional surface wave probe was 0.33 mm on the average, while the decrement in diameter of rolls by grinding by use of the apparatus equipped with the surface wave probe of the invention was 0.2 mm on the average.

As in this experiment, the decrement in diameter of rolls by grinding on the basis of the technique of the invention is lowered by at least 0.1 mm on the average, as compared with that on the basis of the conventional technique. In this connection, we confirmed that when the roll having been ground in that manner on the basis of the technique of the invention was used in rolling sheets, the degree of the surface flaws that appeared in the rolled sheets owing to the small pits formed on the surface of the roll in use was substantially the same as that in the sheets having been rolled by the use of the roll as tested and ground on the basis of the conventional technique.

The invention also provides an ultrasonic test apparatus for detecting flaws in columnar structures, in which a surface wave probe is contacted with the surface of a rotating columnar structure via a coupling liquid medium existing therebetween, and a surface wave is propagated into the columnar structure from the surface wave probe while the probe receives the reflected waves from the flaws existing in and just below the surface of the columnar structure so as to detect the flaws. The apparatus comprises a columnar structure-rotating means for rotating the columnar structure in the circumferential direction of the structure; a rotating speed-monitoring means for monitoring the rotating speed of the columnar structure being rotated by the columnar structure-rotating means; a holder means for holding the surface wave probe above the columnar structure to ensure a predetermined distance between the probe and the surface of the columnar structure; a scanning means for scanning the probe in the axial direction of the structure; a couplant supply means capable of supplying a liquid medium to be a coupling medium for ultrasonic waves to the gap between the surface wave probe and the surface of the columnar structure and provided with a flow control valve capable of controlling the flow rate of the liquid medium in accordance with the rotating speed of the columnar structure to be rotated by the columnar structure-rotating means; a surface wave probe which is provided with a piezoelectric element, a wedge disposed on the front surface of the piezoelectric element and a damping block disposed on the back surface of the piezoelectric element, so that, where the center frequency of the surface wave to be transmitted and received by the probe is fc in the frequency spectrum, the frequency bandwidth within which the spectrum magnitude falls the range between the peak value and the peak value–6 dB covers at least 0.50 fc or larger, and that the probe is capable of detecting the flaws in the columnar structure using surface waves; an ultrasonic pulser/receiver capable of supplying to the surface wave probe, an electric pulse for producing a surface waves and capable of amplifying the signals which the surface wave probe has received to a level necessary for flaw detection and outputting it; a gating means for extracting the signals for flaw detection from the signals which the ultrasonic pulser/receiver has outputted, and outputting them; and a peak detector/comparator means for detecting the amplitude of the signals which the gating means has outputted, and outputting the thus-detected signals, or for comparing the level of the signals which the gating means has outputted with a predetermined threshold voltage and, when the level of the thus-compared signals is large, outputting signals that indicate the presence of flaws in the structure being tested. The apparatus of the invention has attained the above-mentioned third subject matter.

In particular, in the apparatus noted above where one surface of the wedge of the probe is so inclined that the normal line relative to the inclined surface intersects the normal line relative to the bottom surface of the wedge to be contacted with the surface of the columnar structure to be tested via a coupling medium existing therebetween at an incident angle θi to be defined by the above-mentioned formula (3) and where the front surface of the piezoelectric element of the probe is attached to the thus-inclined surface of the wedge, the surface waves having been transmitted by the probe can be well propagated into the surface of the columnar structure.

We, the present inventors further carried out still another test experiment using a high-speed tool steel roll having artificial flaws therein. In the experiment, the rotating speed of the roll was varied, and a varying amount of a coupling liquid medium (as the medium, water was used in the experiment) was applied to the rotating roll in order to determine the suitable amount of the coupling medium via which the ultrasonic wave having been produced by the probe could be stably transmitted into the roll surface without any surplus liquid medium flowing ahead of the probe, and the height of the reflected waves from the artificial flaws could be kept constant. The data obtained in the experiment are shown in FIG. 6. Where the amount of the medium (water) falls within the range as shadowed in the graph of FIG. 6, the ultrasonic waves from the probe are stably transmitted to the roll surface. From the data obtained, it is known that, with the increase in the rotating speed of the high-speed tool steel roll being tested, the amount of the liquid medium to be supplied to the rotating roll must be increased. Accordingly, when the rotating speed of the high-speed tool steel roll being tested is monitored by means of a rotating speed monitor and the amount of the liquid medium to be supplied to the roll is controlled in accordance with the rotating speed of the roll by means of the flow control valve as provided to the couplant supply means, then a suitable amount of the coupling liquid medium can be supplied to the gap between the probe and the surface of the roll. In that manner, the transmission of the ultrasonic wave from the probe into the roll surface is stabilized, and any surplus liquid medium is prevented from flowing ahead of the probe.

To attain the above-mentioned third subject matter, the invention further provides a method of grinding a roll of which the surface has been thermally/mechanically damaged. In the invention, a surface wave probe is contacted with a roll to be ground or being ground, via a membrane of a coupling medium existing therebetween, while the roll is rotated, so that surface waves from the probe is propagated into the roll surface while removing the liquid from the path of surface waves, and the height of the reflected waves from the thermally/mechanically damaged parts existing or remaining in the surface of the roll is measured, and the grinding allowance of the roll is determined in accordance with the thus-measured height of the reflected waves.

The surface wave probe for roll testing in the invention is contacted with the surface of a rotating roll via a coupling medium existing therebetween, and this comprises at least a piezoelectric element and a wedge that introduces the ultrasonic wave from the piezoelectric element into the roll surface at an incident angle $\theta i$. In the invention, the probe is so disposed that it produces the surface waves into the roll surface and detects the flaws existing in and just below the roll surface using the thus-produced surface waves. In this, the incident angle $\theta i$ is defined to satisfy the following formula (4), by which the above-mentioned subject matter is attained.

$$\theta i = \sin^{-1}(CW/CRav) \tag{4}$$

wherein CW indicates the velocity of the ultrasonic wave in the wedge, and

CRav indicates the mean value of the velocity of the surface wave traveling in each roll to be tested.

The incident angle $\theta i$ is an angle to the plane vertical to the roll surface.

To attain the above-mentioned subject matter, the invention still further provides a method of defining the incident angle for a surface wave probe for roll testing, in which the probe is contacted with the surface of a rotating roll via a coupling medium existing therebetween, and this comprises at least a piezoelectric element and a wedge that introduces the ultrasonic wave from the piezoelectric element into the roll surface at an incident angle $\theta i$, while being so disposed that it produces the surface waves into the roll surface and detects the flaws existing in and just below the roll surface using the thus-produced surface waves, and in which the incident angle $\theta i$ is defined to satisfy the above-mentioned formula (4).

Using the surface wave probe, we, the present inventors carried out still another experiment to know the relationship between the height of the reflected waves from the thermally/mechanically damaged parts of a roll and the layer thickness of the still remaining, thermally/mechanically damaged parts of the roll (in the experiment, when the height of the reflected waves measured is lower than the threshold voltage for flaw detection, we say that the remaining layer thickness of the damaged part is zero). In the experiment, we ground rolls that had been thermally/mechanically damaged in rolling operation, little by little, while measuring the height of the reflected waves from the thermally/mechanically damaged parts of each roll to know the relationship noted above. The data we obtained are in FIG. 7, from which it is well known that, with the decrease in the remaining layer thickness of the thermally/mechanically damaged parts of the roll tested, the height of the reflected waves from the thermally/mechanically damaged parts lowers. From the data in FIG. 7, obtained was the relationship between the grinding allowance of the roll for removing the thermally/mechanically damaged parts from the roll, and the height of the reflected waves from the thermally/mechanically damaged parts. This is as shown in FIG. 8. Accordingly, before or during grinding rolls, the height of the reflected waves from the thermally/mechanically damaged parts of each roll is measured by surface wave testing, and the grinding allowance of the roll may be determined according to the relationship as plotted in FIG. 8. In that manner, any overgrinding of the part not mechanically damaged and therefore needless to be removed, and any grinding failure to completely remove the thermally damaged parts can be prevented, and optimum grinding of rolls is possible.

In one preferred embodiment, the surface wave probe and the grindstone are moved to the position of the roll to be ground, at which the height of the reflected waves from the thermally/mechanically damaged parts of the roll is the largest, and the roll is ground by means of plunge grinding while being tested by surface waves. For this, the decrement in diameter of the roll by grinding until the height of the reflected waves from the thermally/mechanically damaged parts reaches a predetermined level or lower is measured and the grinding allowance is determined from the measured decrement. After that the roll is further ground in accordance with the thus-determined grinding allowance. In that manner, the optimum grinding of the roll is realized.

Specifically, before or during grinding them, rolls are subjected to the surface wave testing in the manner as above. Through this testing it is possible to identify the position of each roll at which the height of the reflected waves from the thermally/mechanically damaged parts is the largest, as the position having a largest layer thickness of the remaining thermally/mechanically damaged parts, as is obvious from the relationship as plotted in FIG. 7. Having known this, a roll may be ground as shown in FIG. 9, in which the grindstone 62 of a roll grinder and the surface wave probe 10 are located to the roll 110 at the same position (relative to the axial direction of the roll) where the height of the reflected waves from the thermally/mechanically damaged parts is the largest. In that condition, the roll 110 is ground by means of plunge grinding until the height of the reflected waves from the thermally/mechanically damaged parts of the roll reaches a predetermined threshold voltage or lower, while being subjected to surface wave testing, and the decrement in diameter of the roll to be thus ground is the grinding allowance for removing the thermally/mechanically damaged parts from the entire surface of the roll. According to the thus-determined grinding allowance, the entire surface of the roll may be ground.

BEST MODES FOR CARRYING OUT THE INVENTION

Embodiments of the invention are described in detail hereinunder, with reference to the drawings.

Figure 10:
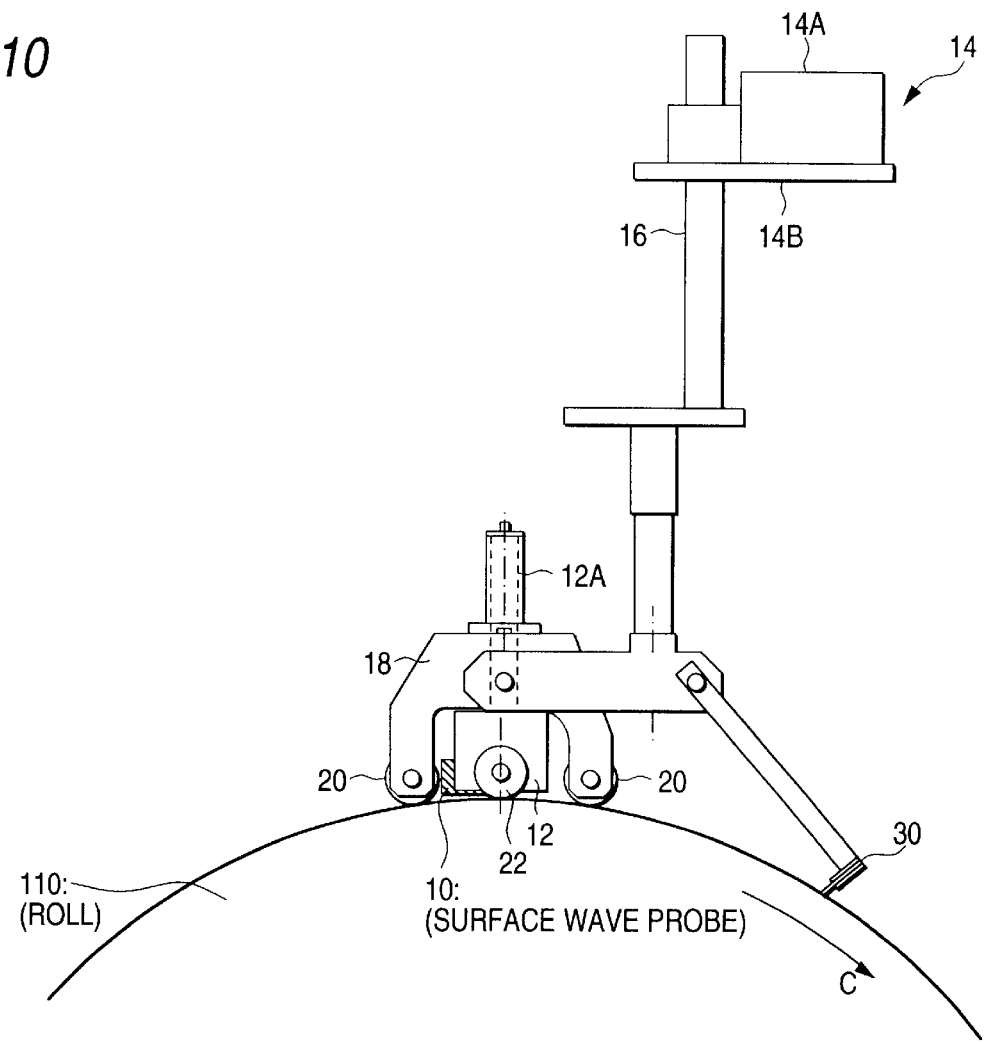
FIG. 10 is a side view showing the outline of the constitution of the first embodiment of the ultrasonic test apparatus of the invention.

FIG. 10 is a side view showing the outline of the constitution of the first embodiment of the ultrasonic test apparatus of the invention.

The ultrasonic test apparatus of this embodiment is for testing the roll 110, and its basic constitution comprises a roll rotating device for rotating the roll 110, a surface wave probe 10 for transmitting and receiving the surface waves in the roll 110, a probe holder 12 for holding the probe 10, and a couplant supply means for supplying a coupling liquid medium (water) to the gap between the surface of the roll 110 and the surface wave probe 10. The supply means is connected with the holder 12, and this will be described hereinunder.

For simplifying the drawing, the roll rotating device is not shown therein. This may be any known one, provided that it acts to rotate the roll 110 to be tested in the circumferential direction C of the roll.

For the surface wave probe 10, the type of the piezoelectric element and the composition of the damping block are so designed that the probe 10 can transmit and receive a surface wave having a frequency bandwidth of at least 0.50 fc or larger and having a pulse length of at most 2.5 times the wavelength of the surface wave.

The surface wave probe 10 is so disposed relative to the roll 110 to be tested that the gap between the probe 10 and the roll 110 could be filled with water (coupling liquid medium). In that condition, an ultrasonic wave is transmitted into the surface of the roll 110 via water to produce surface waves that is propagated into the surface of the roll 110, and the probe 10 receives the reflected waves to detect the surface flaws in the roll 110.

The probe holder 12 holds the surface wave probe 10, and is supported by the supporting member 18 as fitted to the lower part of the guide 16, and the guide 16 is slidable up and down relative to the fixing member 14 as positioned above the roll 110. The supporting member 18 is provided with a pair of rollers 20 at its front and back, and the rollers 20 total four. Between those rollers 20, disposed is the probe holder 12. When the apparatus is operated for roll testing, these four rollers 20 are rotated while being kept in contact with the surface of the roll 110 so as to stabilize the test scanning.

The fixing member 14 is provided with a motor 14A which is to supply power for sliding up and down the supporting member 18 along the guide 16, through a known mechanical means (not shown), and with a fitting base 14B for the motor 14A.

The fixing member 14 can be scanned in the axial direction of the roll 110 by a scanning means (not shown), whereby the surface wave probe 10 can be scanned in the axial direction of the roll 110.

The probe holder 12 is fitted to the lower end of the rod member 12A, and the rod member 12A is loosely clamped to the supporting member 18 so that it is movable up and down relative to the member 18. In that condition, the probe holder 12 is supported by the supporting member 18 while it is all the time pressed downward in the drawing, or that is, against the surface of the roll 110 by means of springs (not shown) provided at predetermined positions around the rod member 12A.

The probe holder 12 is provided with a pair of following rollers 22 which are for forming a predetermined gap between the surface wave probe 10 and the roll 110 and which protrude from beneath the surface wave probe 10 toward the roll 110.

Figure 11:
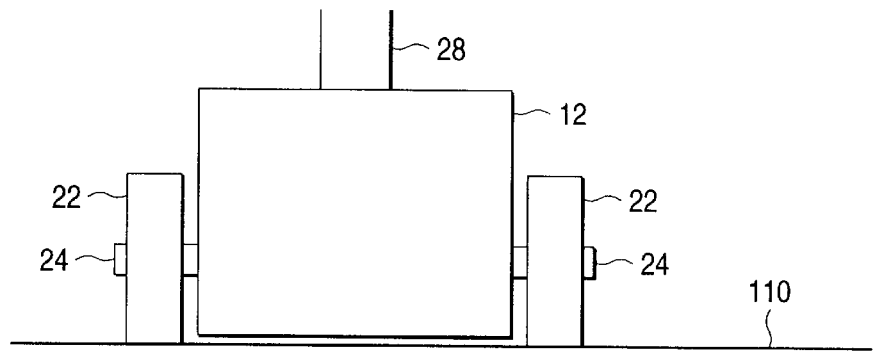
FIG. 11 is an enlarged front view showing the probe holder part in the first embodiment.

FIG. 11 is an enlarged front view showing the condition, in which shafts 24 are disposed at the both opposite sides of the probe holder 12 in the horizontal direction (that is, in the axial direction of the roll 110), and each of the above-mentioned following rollers 22 is rotatably fitted to each shaft 24. In that manner, the following rollers 22 as pivoted on the probe holder 12 receive suitable pressing force from the above-mentioned springs and are all the time kept in contact with the surface of the roll 110 while the roll 110 is tested. According to the constitution of the probe holder 12 noted above, the surface wave probe 10 is held above the roll 110 in such a manner that a predetermined gap is ensured all the time between the probe 10 and the roll 110.

Figure 12:
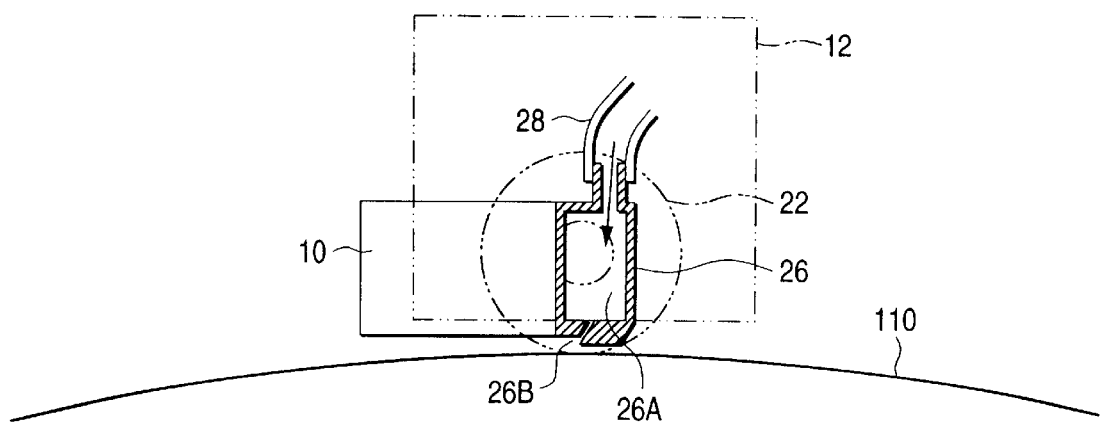
FIG. 12 is a partly-cleaved side view showing the major part of the coupling medium supply part as fitted to the surface wave probe in the first embodiment.

As shown in FIG. 12 in which the details of the probe holder 12 and the following rollers 22 are omitted but their outlines are designated by two-dotted lines, the probe holder 12 is provided with a water supply (water-supplying means) 26 existing inside it. Water having been led through the duct 28 is once stored in the storing body 26A and is let out through the outlet hole 26B formed at the bottom of the storing body 26A. In that manner, a non-bubbling water layer is formed between the surface wave probe 10 and the roll 110. The water supply may be any known conventional one, and the detailed description of its structure is omitted herein.

In FIG. 10, the numeral reference 30 indicates a scraper for scraping water so that water having been supplied from the water supply 26 in the manner noted above is prevented from remaining on the surface of the roll and flowing into path of the surface waves on the roll.

As being designed in the manner described in detail hereinabove, the ultrasonic test apparatus of this embodiment ensures the testing of rolls in a simple manner while water to be a coupling medium for ultrasonic wave propagation through the gap between the surface wave probe 10 and the surface of the roll 110 to be tested and while the probe 10 is scanned and moved on the surface of the roll 110.

According to this embodiment, 500 work rolls (high-speed tool steel rolls) for former stands in finishing train were tested, and the decrement in diameter of each roll by grinding until the height of the reflected waves from primary cracks which are so-called fire cracks reaches a predetermined level or lower was measured. Using another ultrasonic test apparatus equipped with a conventional surface wave probe of which the pulse length is about 5 times the wavelength of the surface wave to be produced, the same rolls were also tested in the same manner. As a result, the decrement in diameter, of each roll by grinding by means of the apparatus equipped with the conventional surface wave probe was 0.33 mm on the average, while the decrement in diameter of each roll by grinding by means of the apparatus of this embodiment was 0.2 mm on the average. As in this experiment, the decrement in diameter of rolls by grinding based on the technique of the invention is lowered by at least 0.1 mm, as compared with that based on the conventional technique. In this connection, it was confirmed that when the high-speed tool steel roll having been ground in that manner on the basis of the technique of the invention was used in rolling sheets, the degree of the surface defects that appeared in the rolled sheets owing to the small pits formed on the surface of the roll in use was substantially the same as that in the sheets having been rolled by the use of the roll as tested and ground on the basis of the conventional technique.

Figure 13:
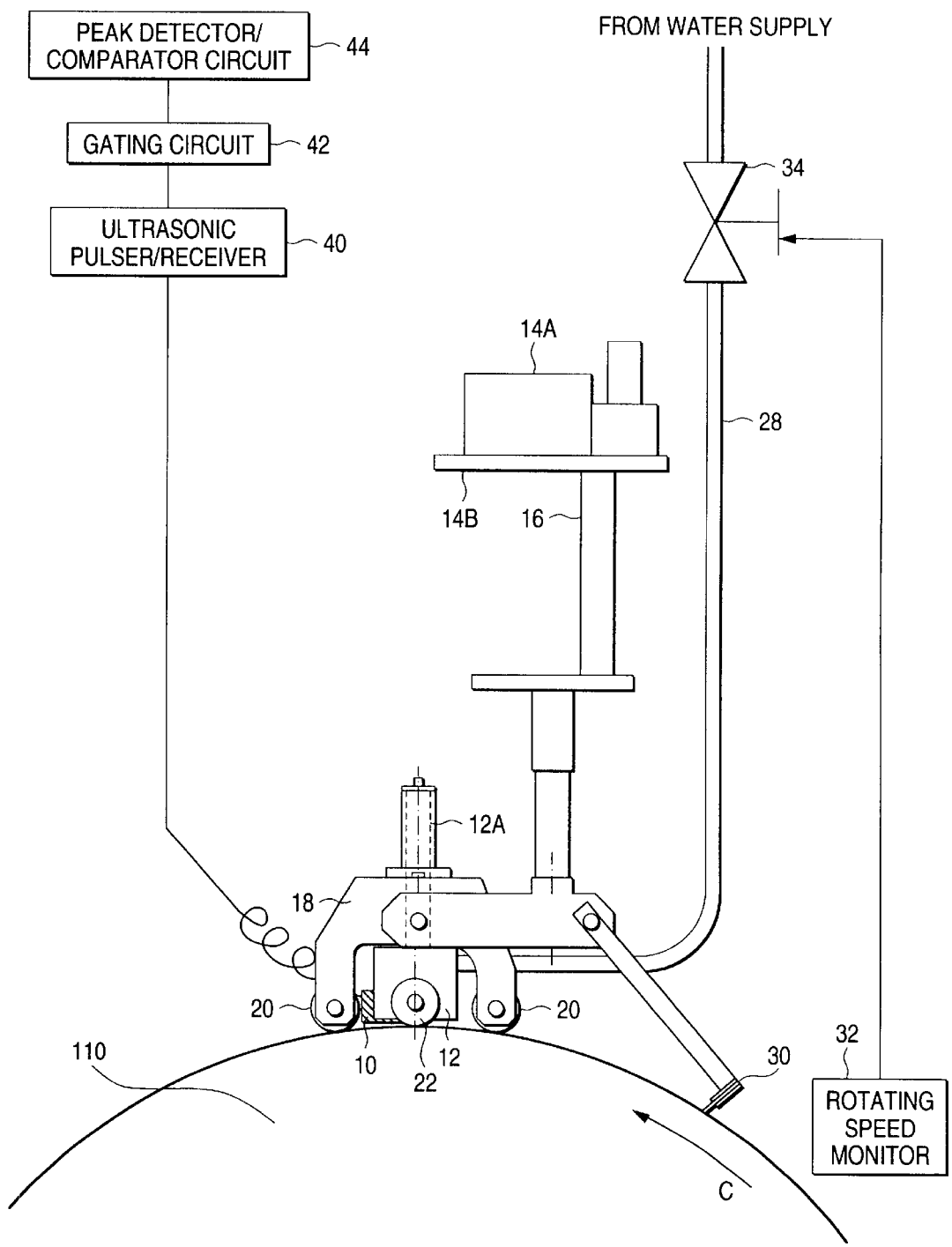
FIG. 13 is a side view showing the outline of the constitution of the second embodiment of the ultrasonic test apparatus of the invention.

Referring to FIG. 13, the second embodiment of the invention that is suitable for testing high-speed tool steel rolls by scanning the surface wave probe 10 on the surface of each roll is described in detail hereinunder.

Figure 1:
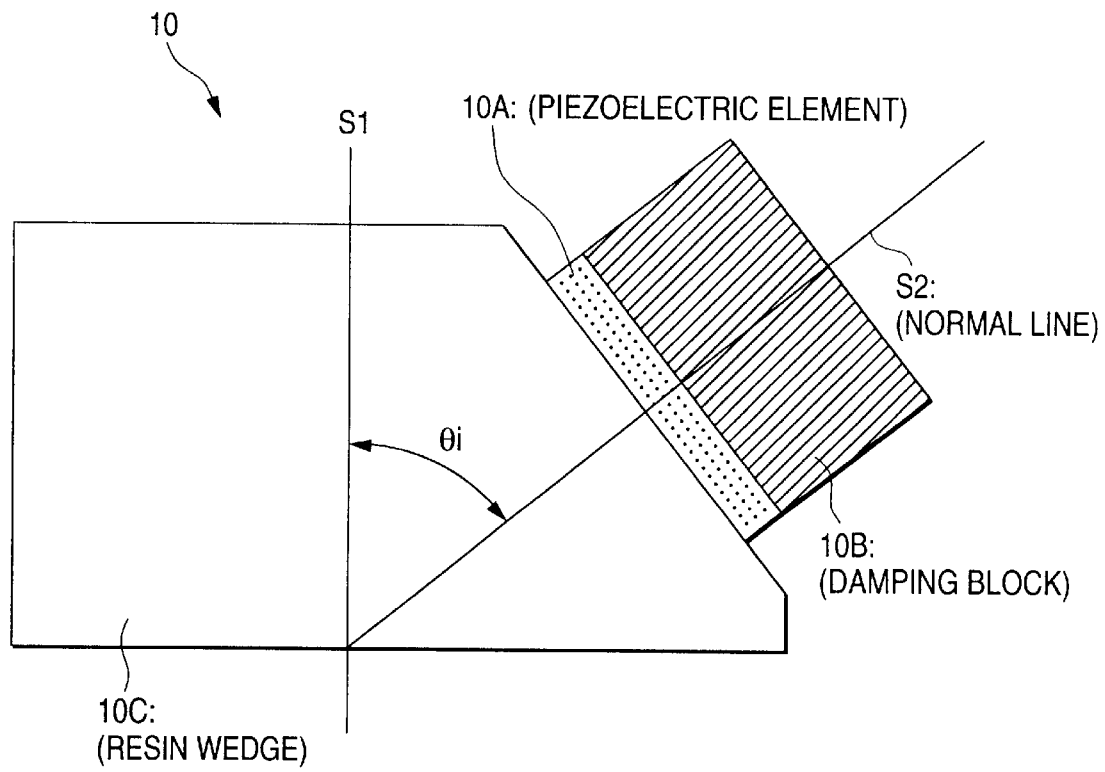
FIG. 1 is an enlarged, cross-sectional view showing the outline of the structure of a surface wave probe to be used in the invention.
Figure 2:
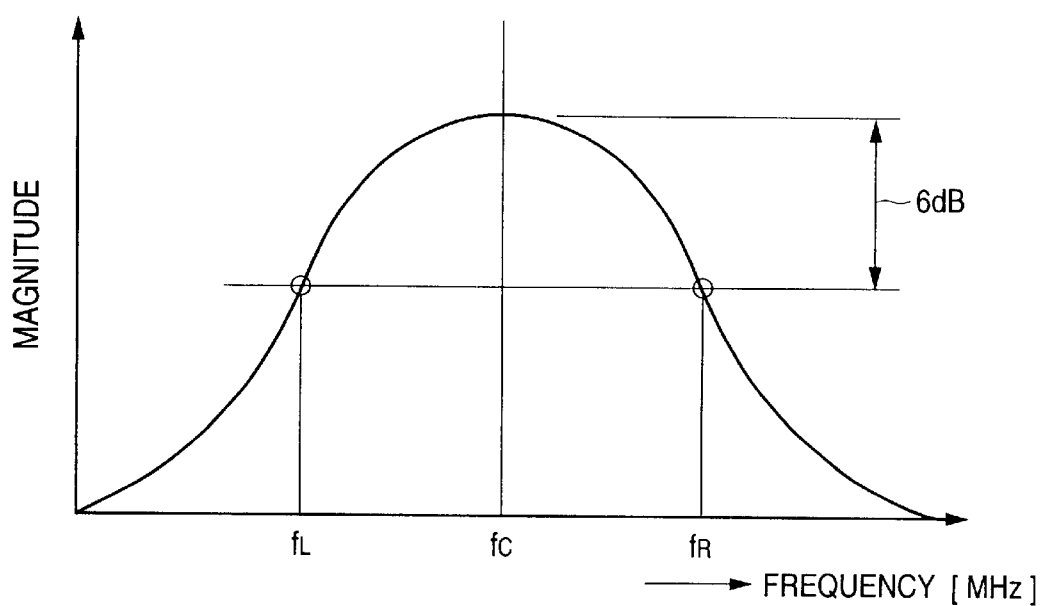
FIG. 2 is a graph for explaining the frequency bandwidth for the surface wave probe.
Figure 3:
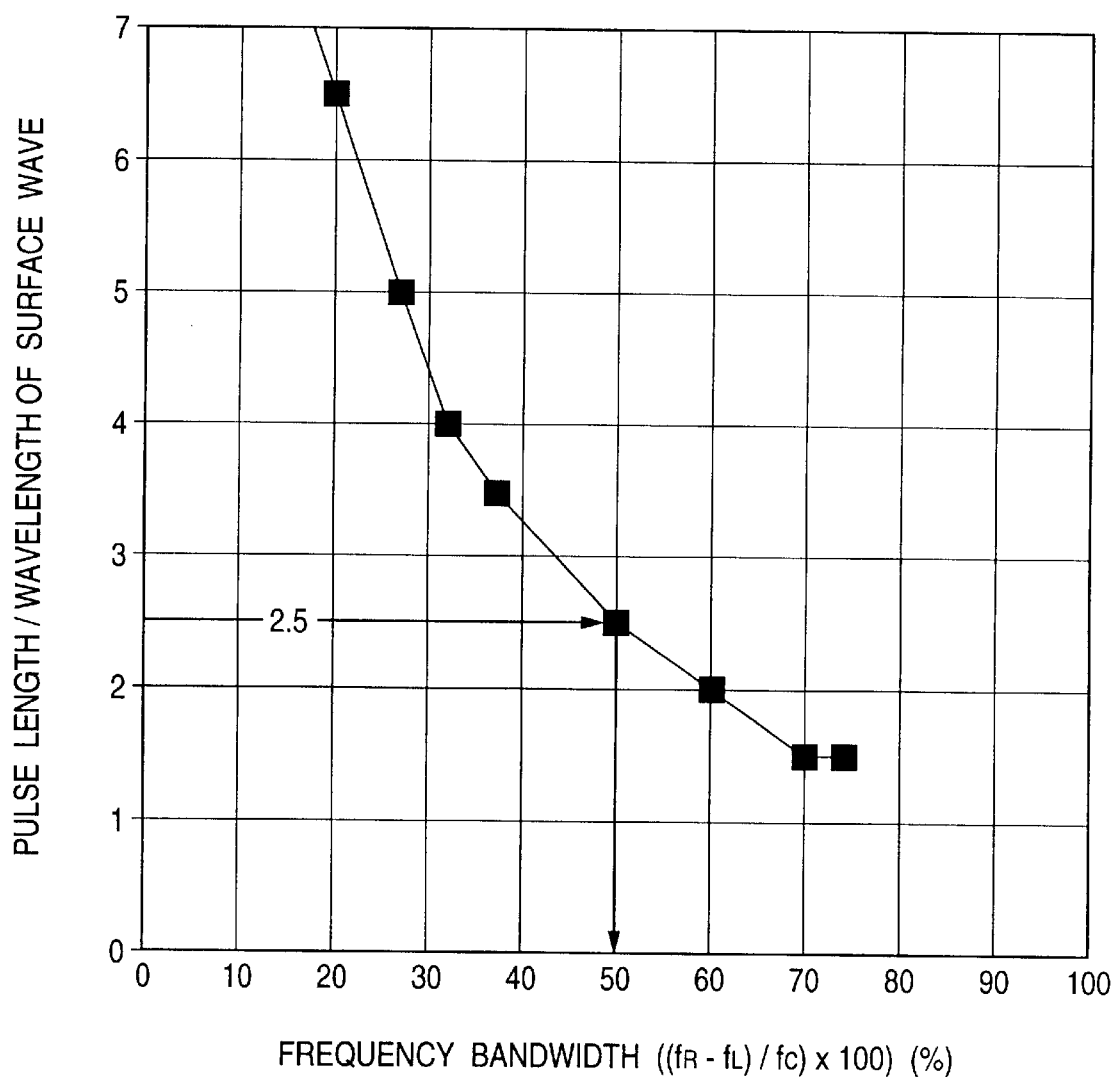
FIG. 3 is a graph showing the relationship between the frequency bandwidth for the surface wave probe and the ratio of (pulse length/wavelength of surface wave).
Figure 4:
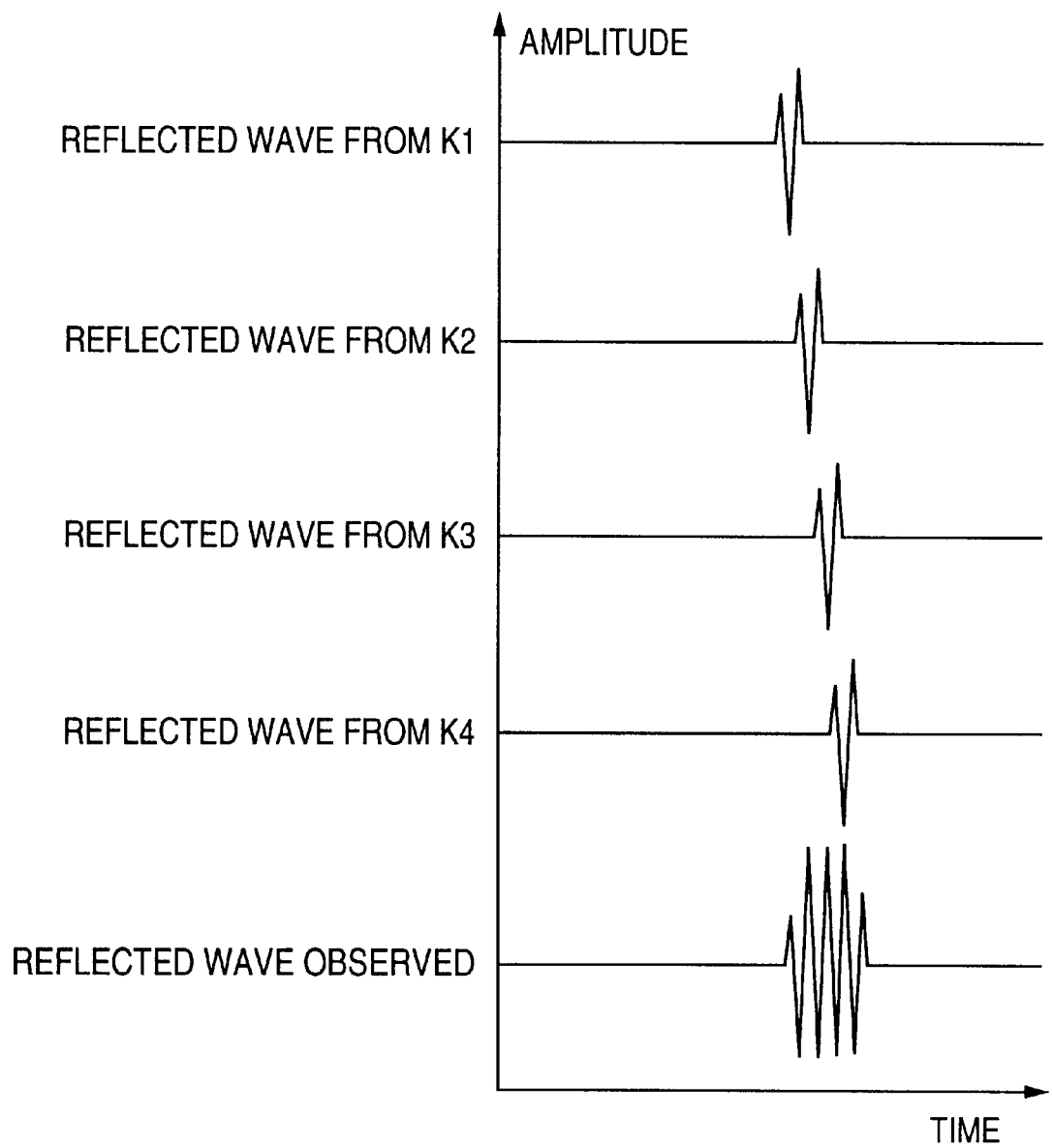
FIG. 4 is an explanatory view indicating the relationship between the waveform to be observed on the basis of the invention, and the reflected waves from small reflectors.
Figure 5:
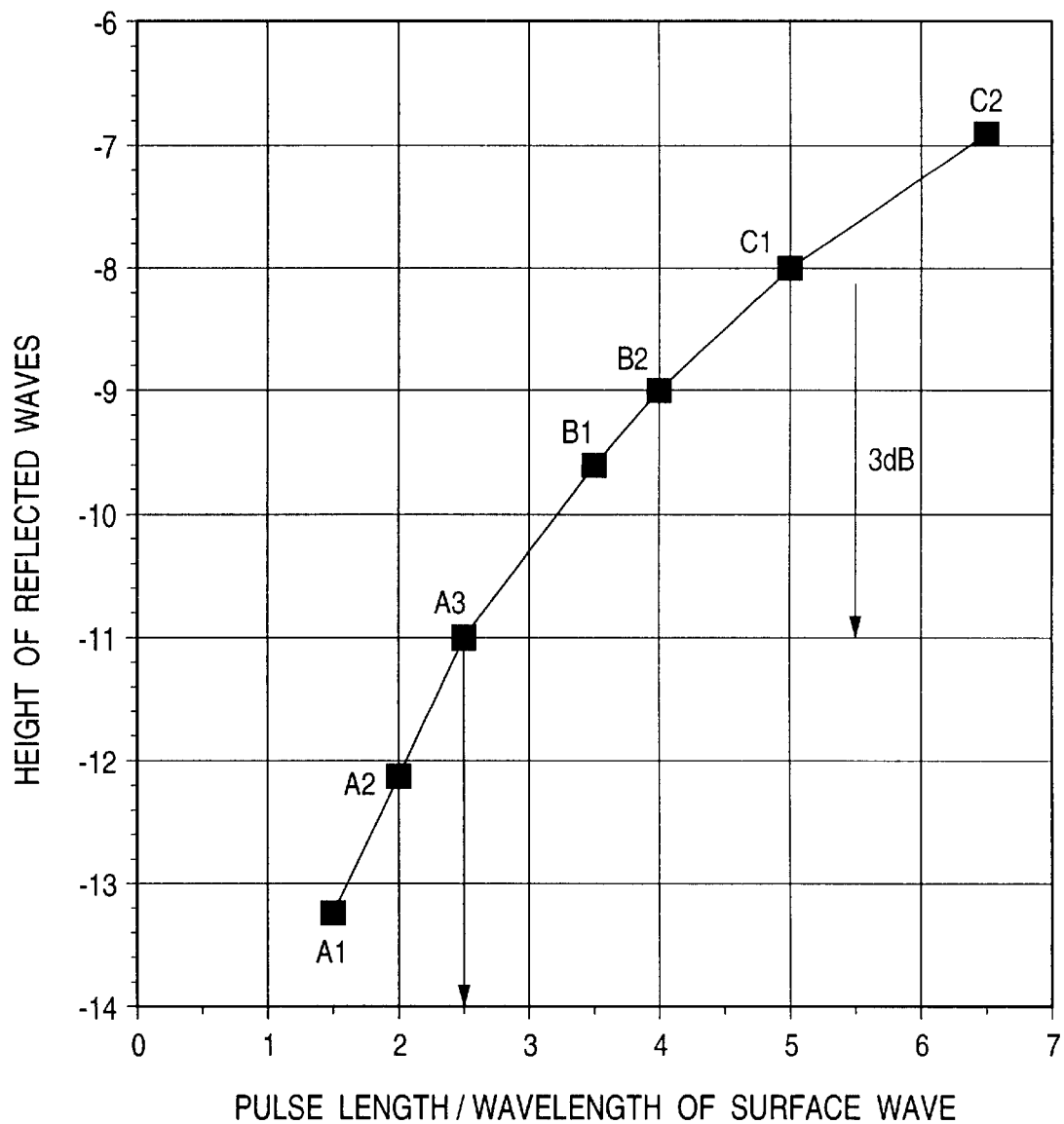
FIG. 5 is a graph showing the relationship between the height of the reflected waves from primary cracks and the ratio of (pulse length/wavelength of surface wave).
Figure 6:
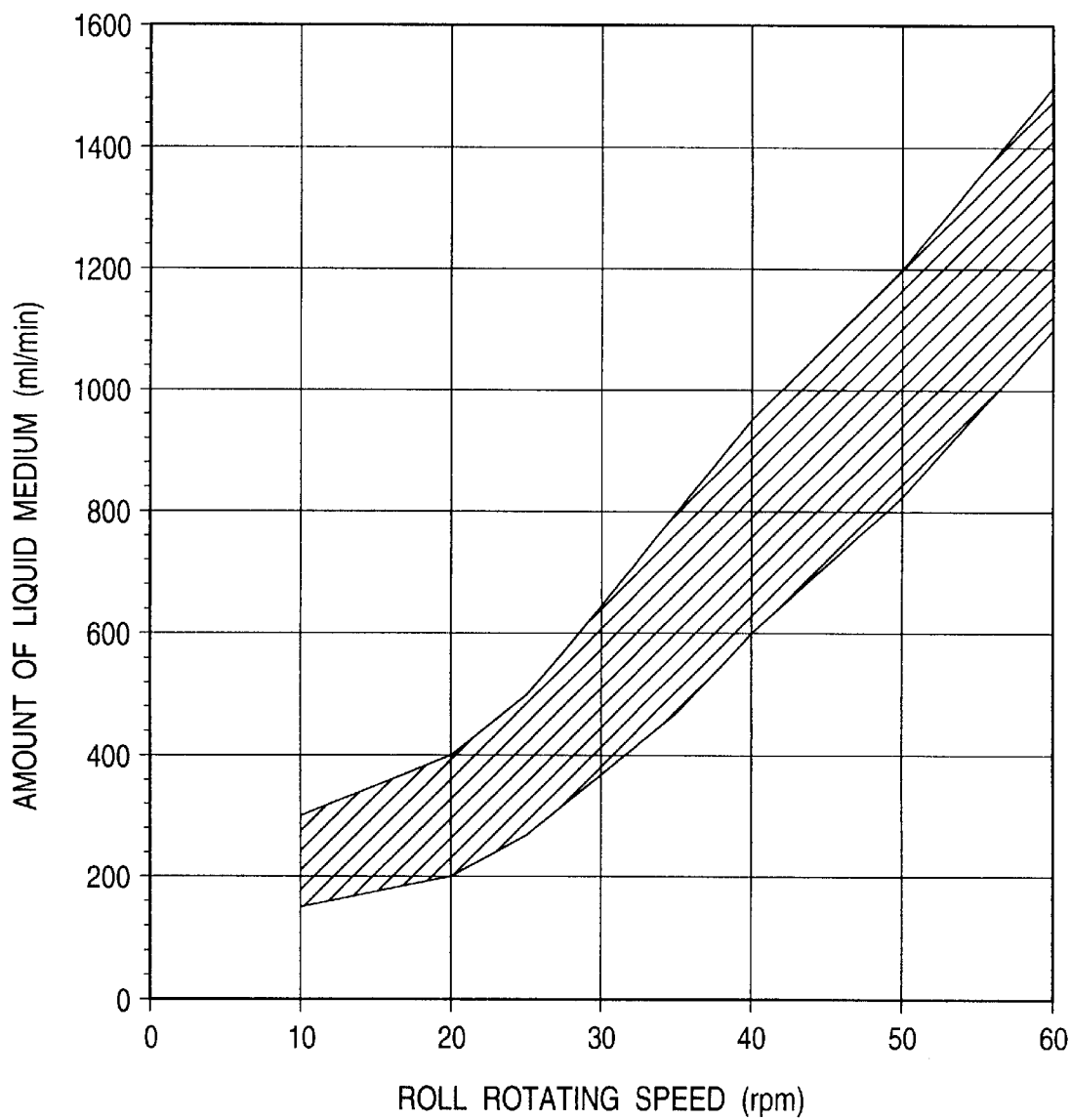
FIG. 6 is a graph showing the relationship between the rotating speed of a roll and a preferred amount of the coupling liquid medium to be supplied to the gap between the probe and the roll, which is for explaining the principle of the invention.
Figure 7:
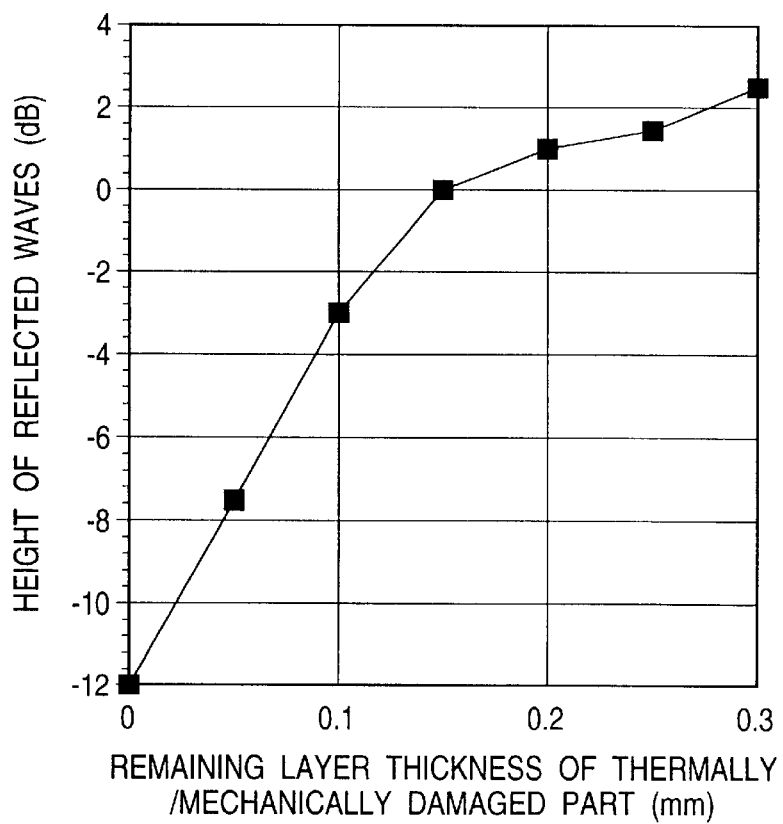
FIG. 7 is a graph showing the relationship between the height of the reflected waves from thermally/mechanically damaged parts of a roll and the remaining layer thickness of the thermally/mechanically damaged parts, which is also for explaining the principle of the invention.

In this embodiment, the roll 110 is a high-speed tool steel roll, and the rotating speed of the roll is, monitored by the rotating speed monitor 32. The data thus monitored are transmitted to the flow control valve 34 connected with the water supply, and the water flow rate is so controlled as to be within the preferred range as in FIG. 6. The signals outputted by the surface wave probe 10 are inputted into the peak detector/comparator circuit 44 processed by the ultrasonic pulser/receiver 40 and the gating circuit 42 in that order.

The ultrasonic pulser/receiver 40 is to supply an electric pulse to the surface wave probe 10 for producing the surface waves. In this pulser/receiver 40, the signals having been received by the surface wave probe 10 is amplified to a level necessary for flaw detection, and are outputted to the gating circuit 42. In the gating circuit 42, the signals for flaw detection are extracted from the signals having been outputted from the ultrasonic pulser/receiver 40, and are outputted to the peak detector/comparator circuit 44. In the peak detector/comparator circuit 44, the peak amplitude of the signals having been outputted from the gating circuit 42 is detected, and the thus-detected signal is outputted from it; or in this, the level of the signals from the gating circuit 42 is compared with a predetermined threshold voltage and, when the level of the thus-compared signal from the gating circuit 42 is large, signals that indicate the presence of flaws in the roll being tested is outputted from the peak detector/comparator circuit 44 Being operated in that manner, the apparatus of this second embodiment detects the flaws in rolls being tested.

Like that in the first embodiment, the probe holder 12 in the second embodiment is provided with a water supply 26 in its inside as shown in FIG. 12. The flow rate of water from the water supply 26 is controlled by the flow control valve 34 according to the rotating speed (peripheral speed) of the roll 110. In the water supply 26, water having been led through the duct 28 is once stored in the storing body 26A and is let out through the outlet hole 26B formed at the bottom of the storing body 26A. In that manner, a non-bubbling water layer is formed between the surface wave probe 10 and the roll 110.

The others in this embodiment are the same as those in the first embodiment noted above and are designated by the same reference numerals as in the first embodiment. The detailed description of these others is omitted herein.

Figure 14:
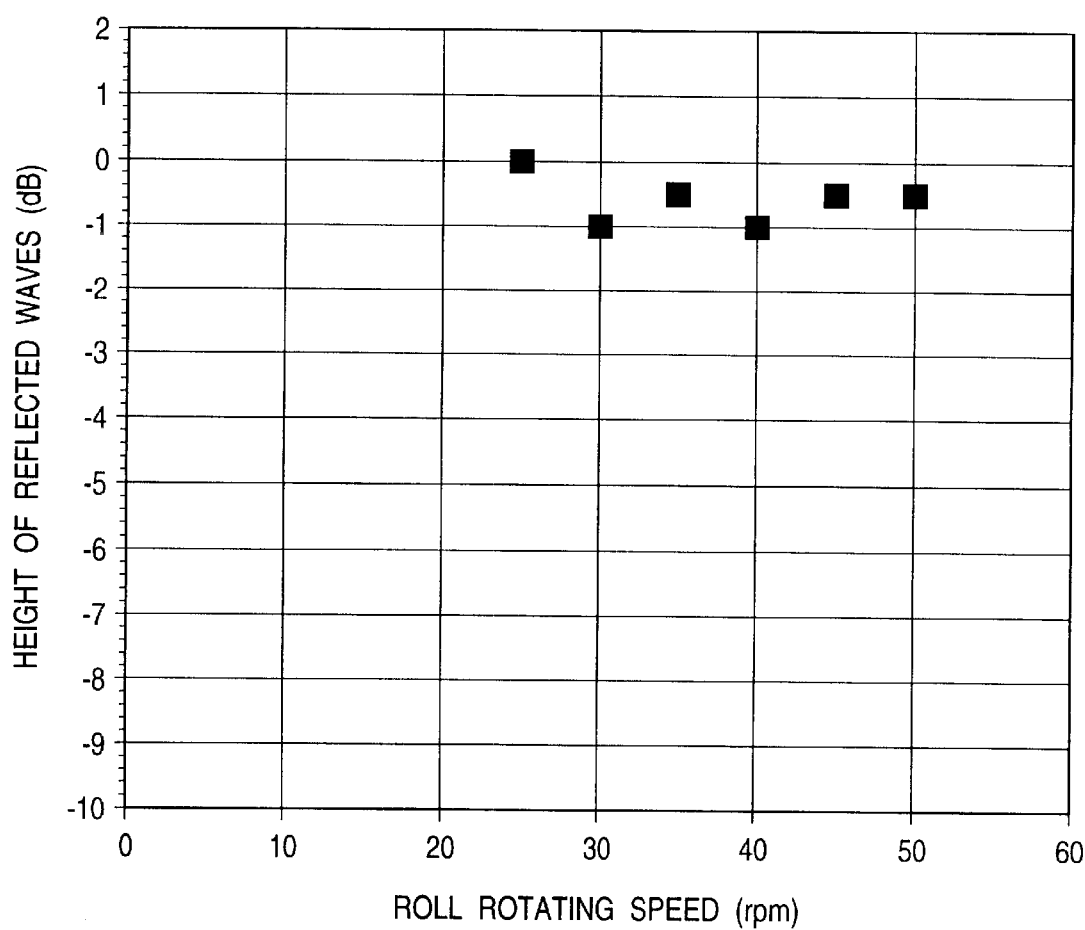
FIG. 14 is a graph showing the data of an experiment for the second embodiment relative to the relationship between the height of the reflected waves from the flaws and the rotating speed of a roll, for which the rotating speed of the roll was varied for flaw detection according to the second embodiment.

High-speed tool steel rolls having surface flaws were tested by use of the apparatus of this embodiment, while their rotating speed was varied from 25 rpm to 50 rpm. The data obtained for the relationship between the height of the reflected waves from the flaws and the rotating speed of each roll are shown in FIG. 14. From these, it is known that the apparatus of this embodiment well detect the surface flaws in the high-speed tool steel rolls tested, irrespective of the rotating speed of the rolls.

Figure 15:
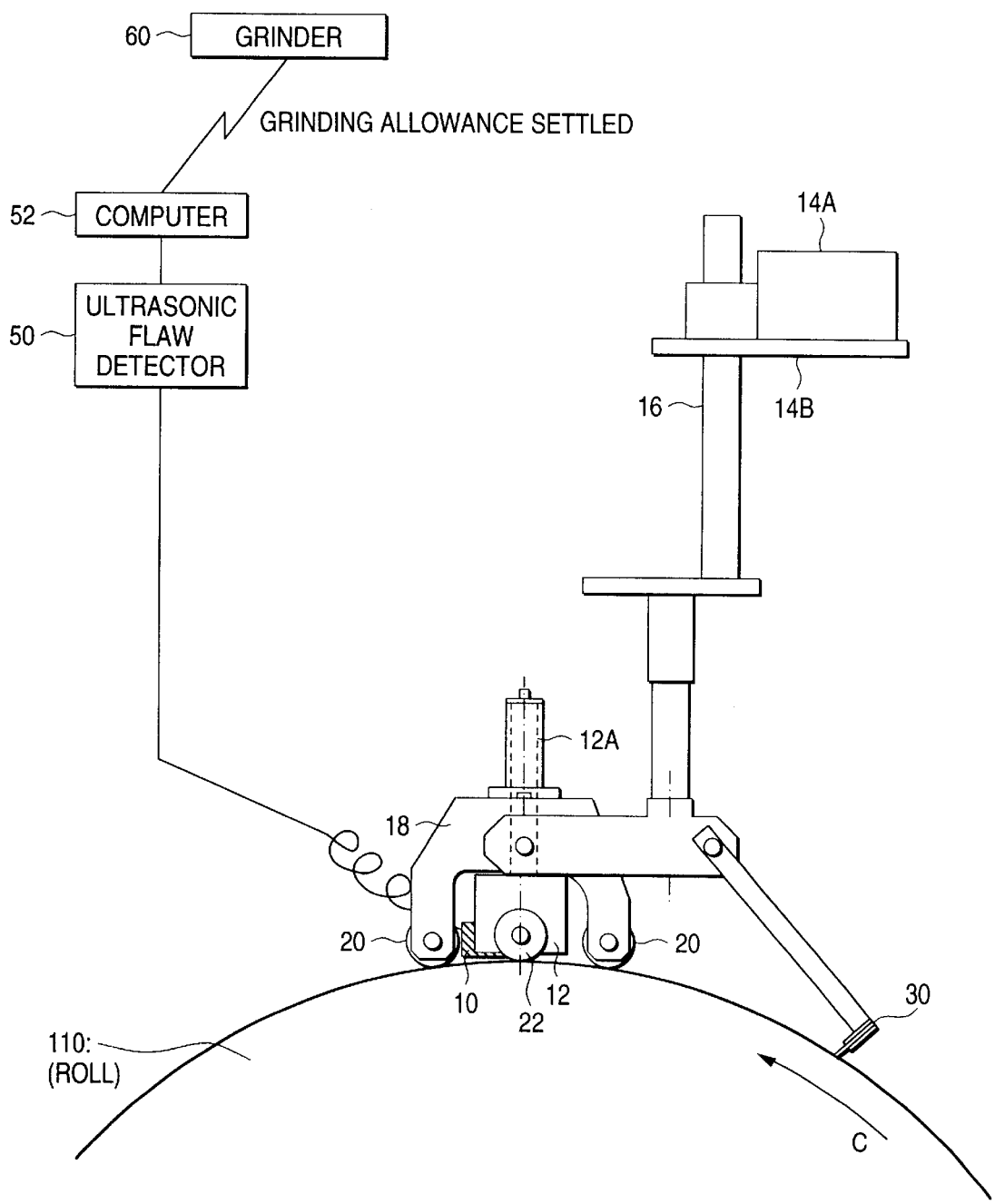
FIG. 15 is a side view showing the outline of the constitution of the third embodiment of the ultrasonic test apparatus of the invention.

Next, referring to FIG. 15, the third embodiment of the invention is described in detail hereinunder.

In this embodiment, rolls to be ground or being ground are tested by means of surface waves. Specifically, in the apparatus of this embodiment, the height of the reflected waves from thermally/mechanically damaged parts of the roll 110 is measured, and the grinding allowance for the roll 110 to be ground is transmitted to the grinder 60 in which the roll 110 is ground. The grinder may be any known conventional one, and is not shown for simplifying the drawing.

Figure 8:
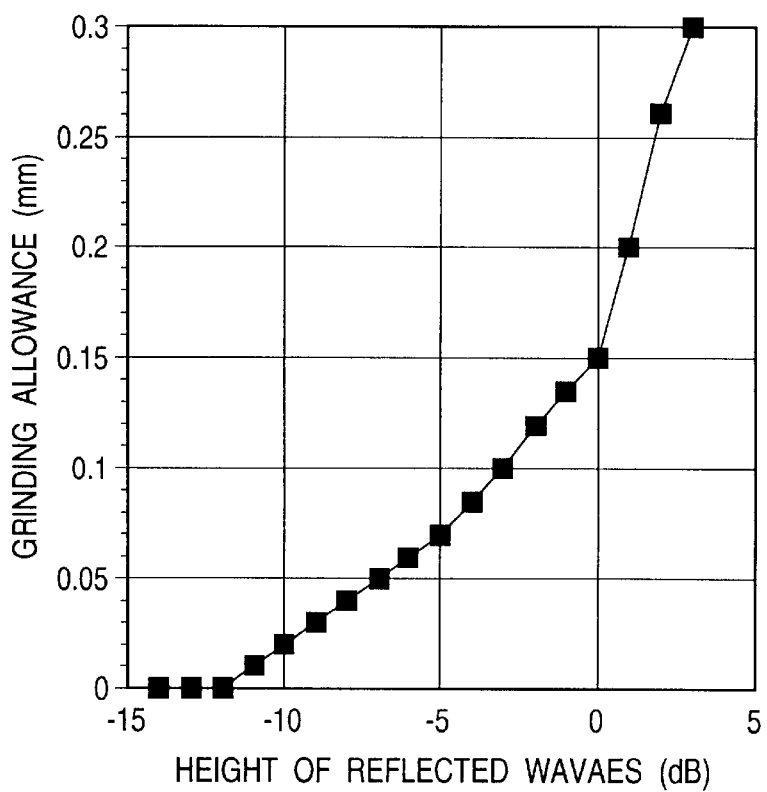
FIG. 8 is a graph showing the relationship between the grinding allowance of a roll and the height of the reflected waves from thermally/mechanically damaged parts of the roll, which is also for explaining the principle of the invention.

The surface wave probe 10 is connected with the ultrasonic flaw detector 50, and an electric pulse is supplied to the surface wave probe 10 from which the surface wave produced is transmitted into the roll 110. In the ultrasonic flaw detector 50, the signals which the surface wave probe 10 has received and outputted to the ultrasonic flaw detector 50 are amplified to a level suitable to flaw detection. The ultrasonic ultrasonic flaw detector 50 is provided with a gating circuit (no shown) that may be the same as in the second embodiment, and the reflected waves from the thermally/mechanically damaged parts in the roll 110 are extracted from the amplified signals in the gating circuit. In the ultrasonic flaw detector 50, the height of the thus-extracted, reflected waves is measured. Having been thus measured in the ultrasonic flaw detector 50, the data of the height of the reflected waves from the thermally/mechanically damaged parts are transmitted to the computer 52, in which the grinding allowance for removing the thermally/mechanically damaged parts is determined with reference to the relationship as shown in FIG. 8. The thus-settled data of the grinding allowance are transmitted to the grinder 60, in which rolls are ground with, for example, a grindstone.

The others in this embodiment are the same as those in the first and second embodiments noted above and are designated by the same reference numerals as in them. The detailed description of these others is omitted herein.

According to this embodiment, 200 work rolls for former stands in finishing train were tested, and the decrement in diameter of each roll by grinding was measured. Apart from this, the decrements in diameter of the same rolls by grinding based on a conventional method were presumed from the actual decrements measured. In a conventional method, the rolls are repeatedly ground by a predetermined grinding allowance until the height of the reflected waves from the thermally/mechanically damaged parts becomes lower than a predetermined threshold voltage in the surface wave testing after ground. The above-mentioned actual decrement was measured after the grinding based on the method using the apparatus of this embodiment of the invention. The presumed decrement in diameter in the conventional method was 0.23 mm on the average. As opposed to this, the decrement in diameter by grinding based on the method of the invention for suitable grinding of rolls was 0.18 mm on the average. This means that the decrement in diameter by grinding based on the method using the apparatus of this embodiment is lower by at least 0.05 mm than that based on the conventional method.

Figure 16:
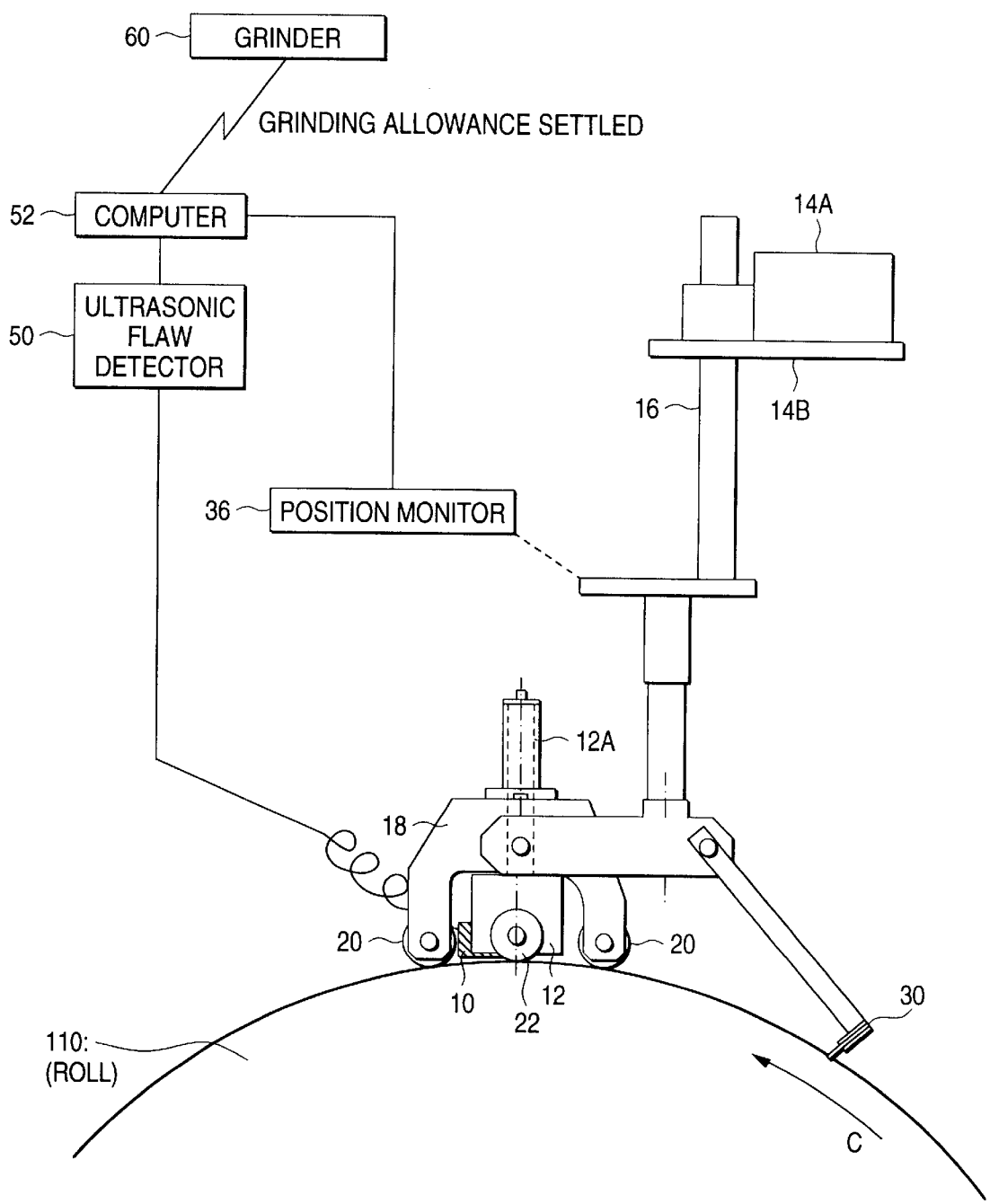
FIG. 16 is a side view showing the outline of the constitution of the fourth embodiment of the ultrasonic test apparatus of the invention.

Next, referring to FIG. 16, the fourth embodiment of the present invention is described in detail hereinunder.

In this embodiment, provided is a position monitor 36 for monitoring the position of the surface wave probe 10 relative to the axial direction of the roll being tested. The data of the position of the surface wave probe 10 having been monitored by the position monitor 36 are transmitted to the computer 52. In surface wave testing of rolls to be ground or being ground according to this embodiment, the position of the surface wave probe 10 that is in contact with the specific place of the roll at which the height of the reflected waves from the thermally/mechanically damaged parts is the largest is determined by the position monitor 36. For so-called plunge grinding based on this embodiment, as shown in FIG. 9, the surface wave probe 10 and the grindstone 62 are mechanically so aligned that the two are to be contacted with the roll 110 at the same position relative to the axial direction of the roll 110.

The others in this embodiment are the same as those in the third embodiment noted above and are designated by the same reference numerals as in the third embodiment. The detailed description of these others is omitted herein.

The operation of this embodiment is described in detail. First, while the roll 110 to be ground or being ground is rotated in its circumferential direction C, the surface wave probe 10 is scanned over the roll 110 in the axial direction of the roll 110. In that manner, the entire surface of the roll 110 is tested by use of the surface waves traveling thereon, and the height of the reflected waves from the thermally/mechanically damaged parts of the roll 110 and also the signal that indicates the position of the surface wave probe 10 are inputted into the computer 52. By the action of the computer 52, the position of the surface wave probe 10 that is in contact with the specific place of the roll 110 at which the height of the reflected waves from the thermally/mechanically damaged parts is the largest is determined.

Figure 9:
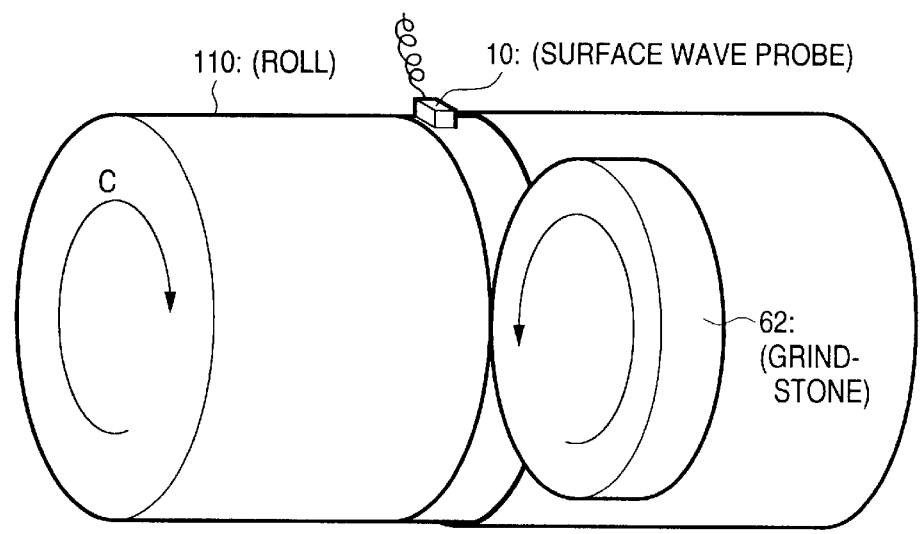
FIG. 9 is a perspective view showing the relationship between the position of the grindstone and that of the surface wave probe in plunge grinding of a roll, which is also for explaining the principle of the invention.

Next, as shown in FIG. 9, the surface wave probe 10 and the grindstone 62 are moved to the thus-determined position of the roll 110, and the roll 110 is ground by means of plunge grinding while being subjected to surface wave testing. The grinding is continued until the height of the reflected waves from the thermally/mechanically damaged parts becomes lower than a predetermined threshold voltage, and the grinding allowance of the roll is thus determined.

The thus-determined grinding allowance is inputted into the grinder 60, in which the remaining surface area of the roll is then ground.

According to this embodiment, 200 work rolls for former stands in finishing train were tested, and the decrement in diameter of each roll by grinding was measured. Apart from this, the decrements in diameter of the same rolls by grinding based on a conventional method were presumed from the actual decrements measured. In a conventional method where the rolls are repeatedly ground by a predetermined grinding allowance until the height of the reflected waves from the thermally/mechanically damaged parts becomes lower than a predetermined threshold voltage in the surface wave testing after ground. The presumed decrement in diameter by grinding based on the conventional method was 0.24 mm on the average. As opposed to this, the decrement in diameter by grinding based on the method of the invention for suitable grinding of rolls was 0.19 mm on the average. This means that, the decrement in diameter by grinding the method using the apparatus of this embodiment is lower by at least 0.05 mm than that based on the conventional method.

Figure 17:
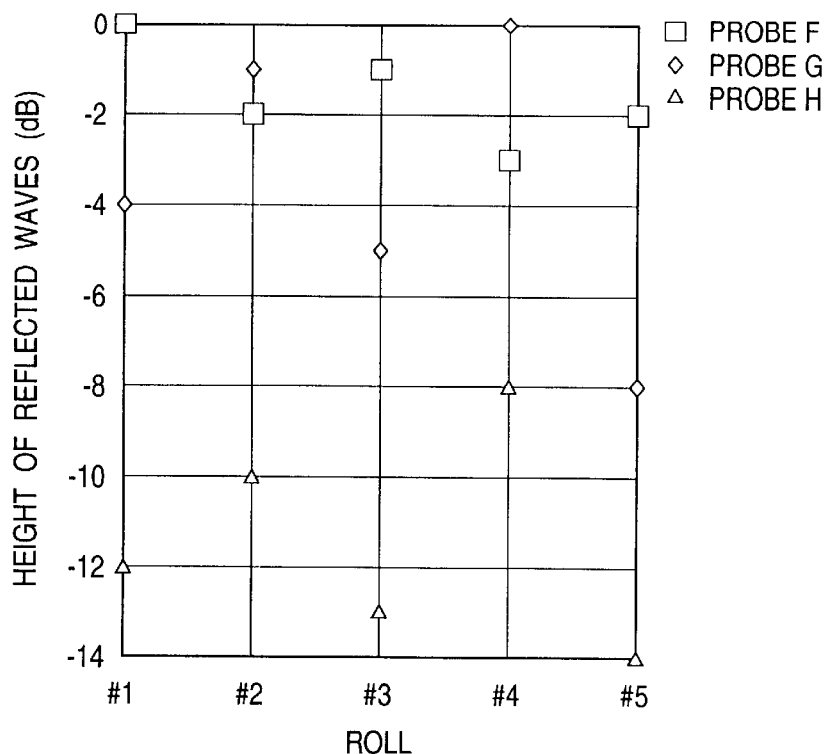
FIG. 17 is a graph showing the data of the height of the reflected waves from artificial flaws in five rolls, for which were used a probe F of the invention and conventional probes G, H.
Figure 18:
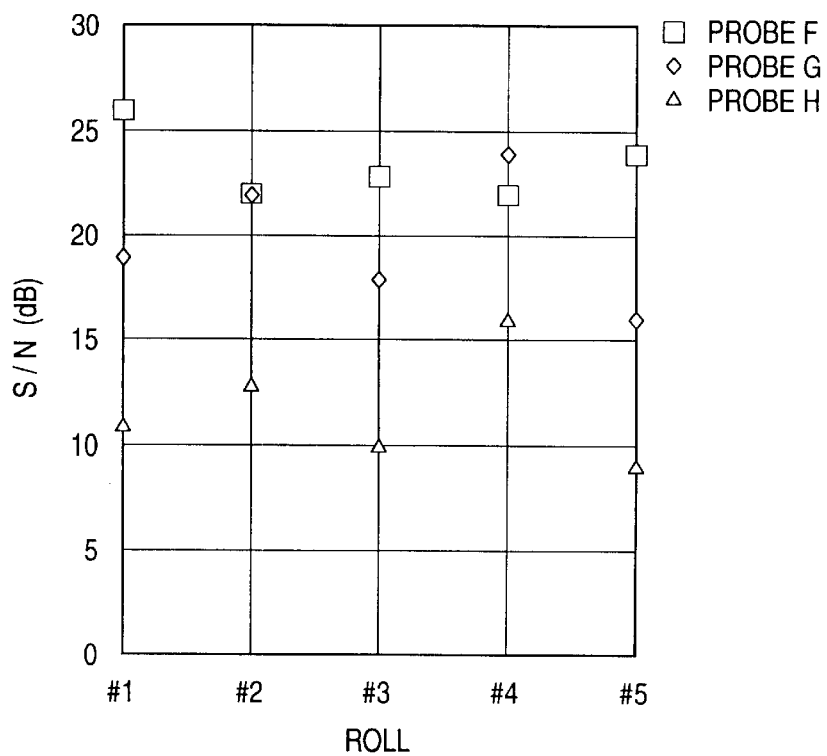
FIG. 18 is a graph showing the data of the signal-to-noise ratio for the reflected waves from artificial flaws in five rolls, for which were used the probe F of the invention and the conventional probes G, H.

Next, referring to FIG. 17 and FIG. 18, the fifth embodiment of the present invention is described in detail hereinunder.

FIG. 17 and FIG. 18 are graphs showing the measuring results of the reflected waves from artificial flaws in five rolls shown in Table 1, for which were used a surface wave probe of the invention and two conventional surface wave probes. FIG. 17 shows the height of the reflected waves from the artificial flaws in those rolls; and FIG. 18 shows the signal-to-noise ratio of the reflected waves from the artificial flaws in those rolls. The flaws were artificially made by drilling each roll toward radial direction to have a diameter of 1 mm and a depth of 1 mm. The wedge of the surface wave probe used herein was of a polystyrol resin (CW=2340 m/sec).

The following three surface wave probes were prepared and used.

Probe F:

For this, the data of the surface wave velocity on the five rolls to be tested were averaged to obtain an average value, CRav. From the value CRav and the ultrasonic wave velocity in the polystyrol resin, CW, obtained was θi according to the formula (2) mentioned above. θi was 48.1 degrees. A surface wave probe was so designed as to meet θi=48.1 degrees. This is Probe F, and this falls within the scope of the invention.

Probe G:

A surface wave probe was so designed as to meet θi=49.2 degrees, which was calculated from the surface wave velocity on Roll #4 in Table 1 and the ultrasonic wave velocity in the polystyrol resin. This is Probe G, and this is a conventional surface wave probe.

Probe H:

A surface wave probe was so designed as to meet θi=51.7 degrees, which was calculated from the surface wave velocity on ordinary steel (2980 m/sec) and the ultrasonic wave velocity in the polystyrol resin. This is Probe H, and this is another conventional surface wave probe.

From FIG. 17 and FIG. 18, it has been verified that Probe F of the invention gives high reflected waves and stable S/N ratios irrespective of the type of rolls to be tested therewith. In FIG. 17, the vertical axis indicates the height of the reflected waves from the artificial flaws with reference to the height of the reflected wave from the artificial flaw on Roll #1 detected by use of Probe F.

Figure 19:
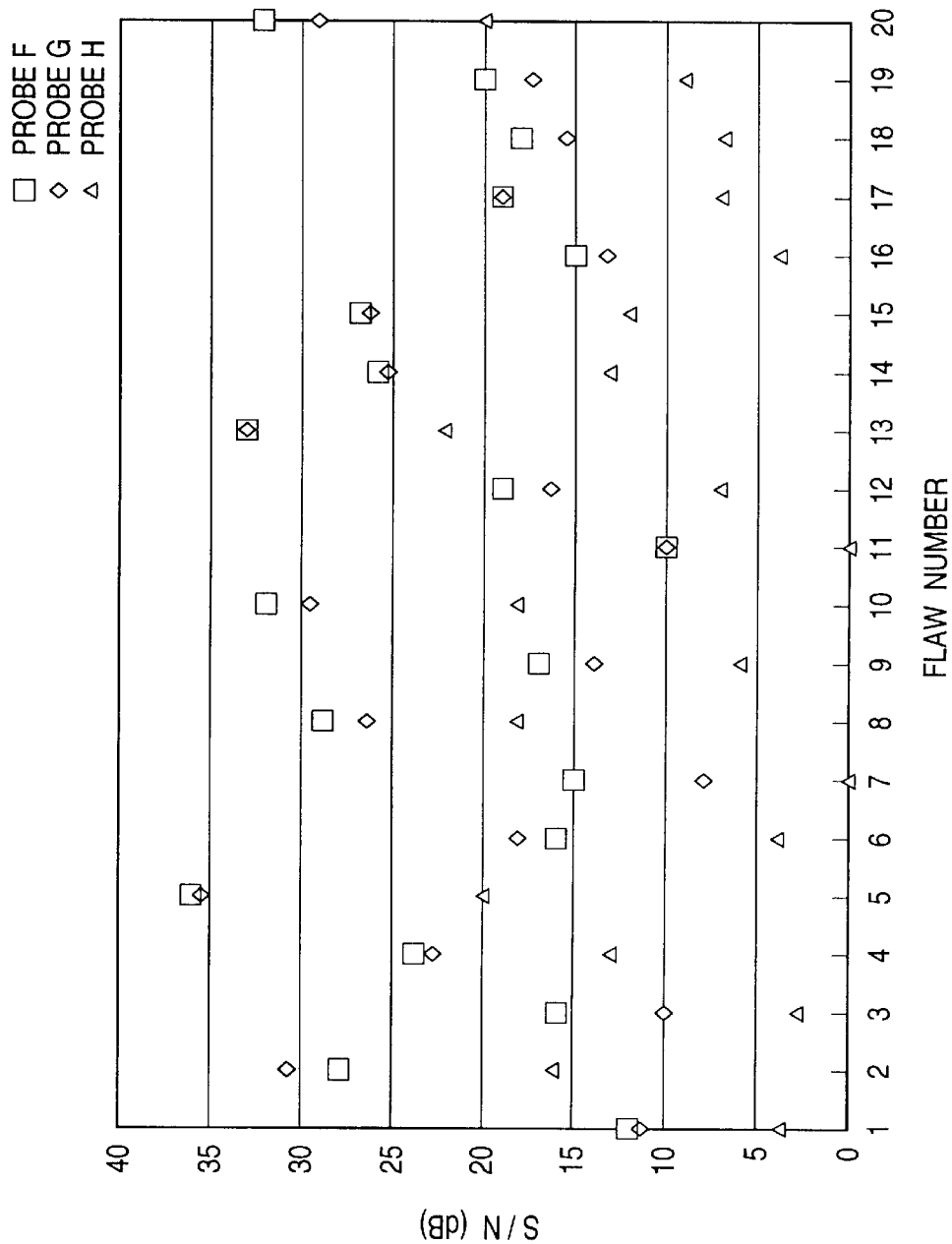
FIG. 19 is a graph showing the data of roll testing for 20 surface flaws, in terms of the signal-to-noise ratio, for which were used the probe F of the invention and the conventional probes G. H.
Figure 20:
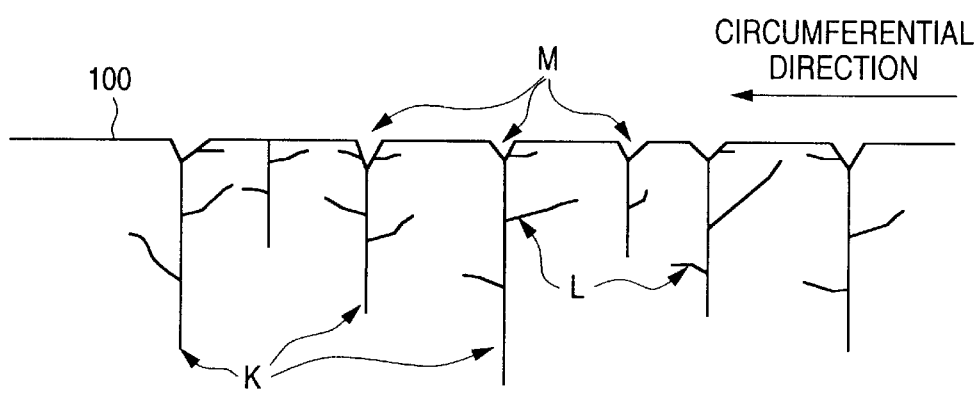
FIG. 20 is a conceptual view for explaining the cracks to be formed in the surface of a work roll for former stands in finishing train, in the circumferential direction of the roll.
Figure 21:
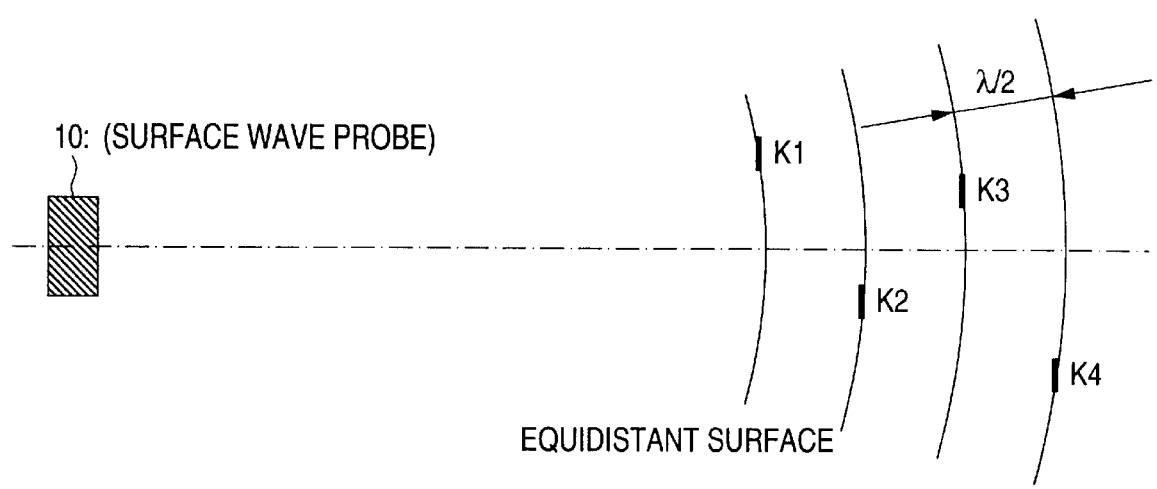
FIG. 21 is an explanatory view showing the relationship between the position of a surface wave probe and that of small reflectors.
Figure 22:
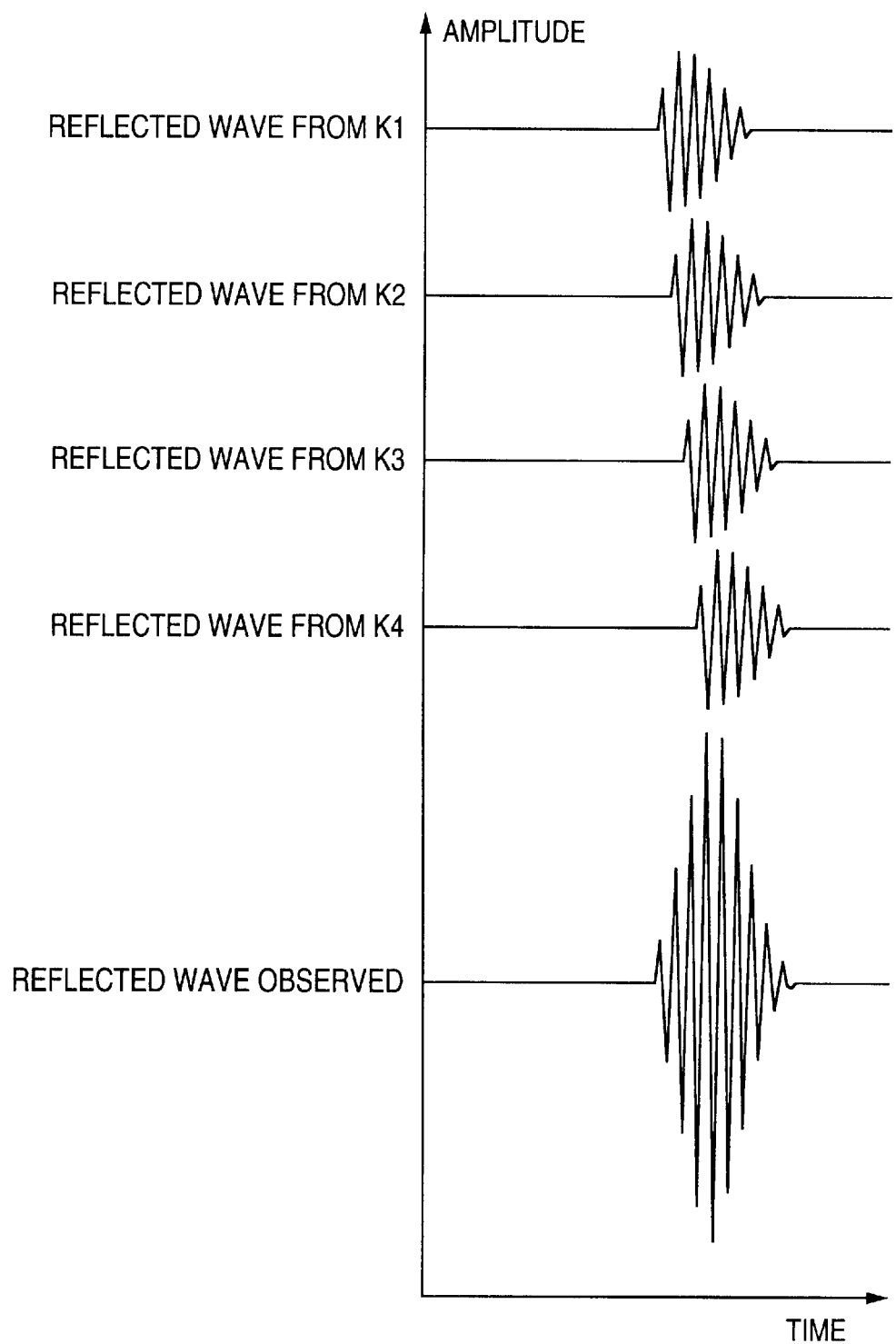
FIG. 22 is an explanatory view indicating the relationship between the waveform to be observed in a conventional method, and the reflected waves from small reflectors.
Figure 23:
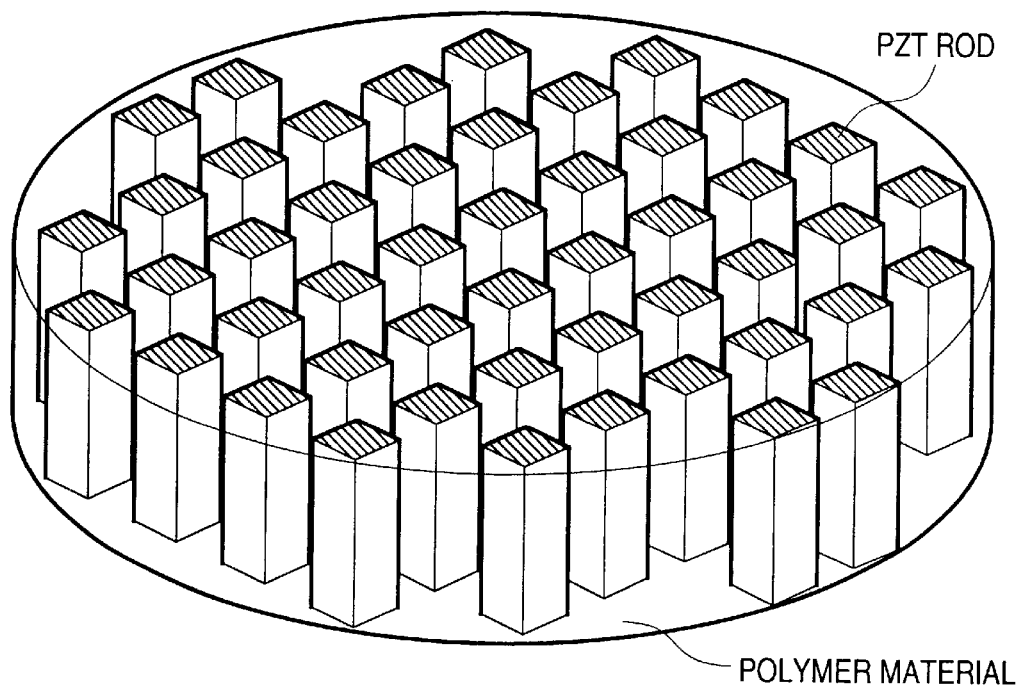
FIG. 23 shows one example of the piezoelectric element for the invention (this is a 1-3 type piezocomposite material).
Figure 24:
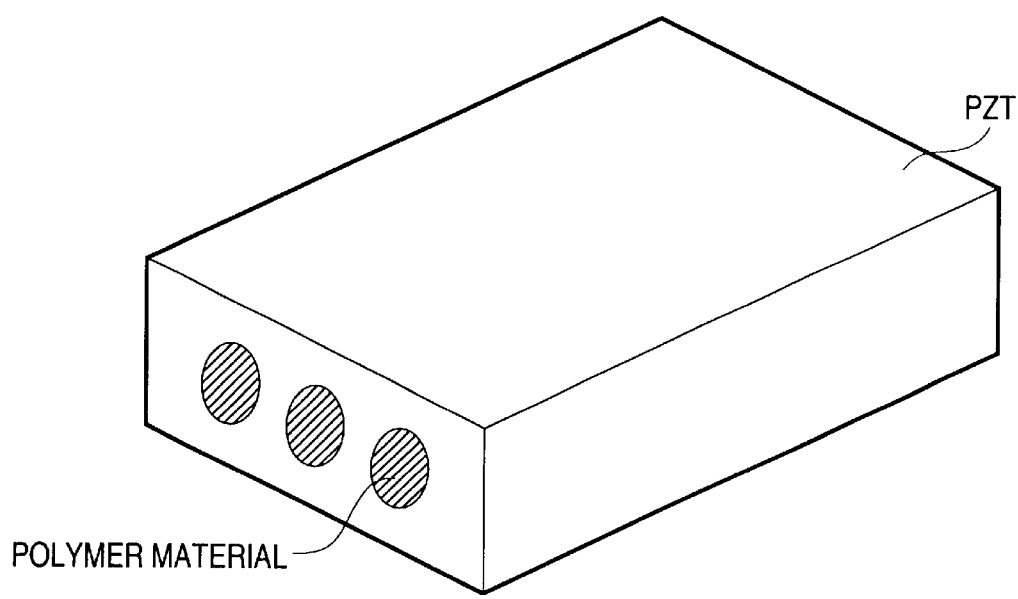
FIG. 24 shows another example of the piezoelectric element for the invention (this is a 3-1 type piezocomposite material).
Figure 25:
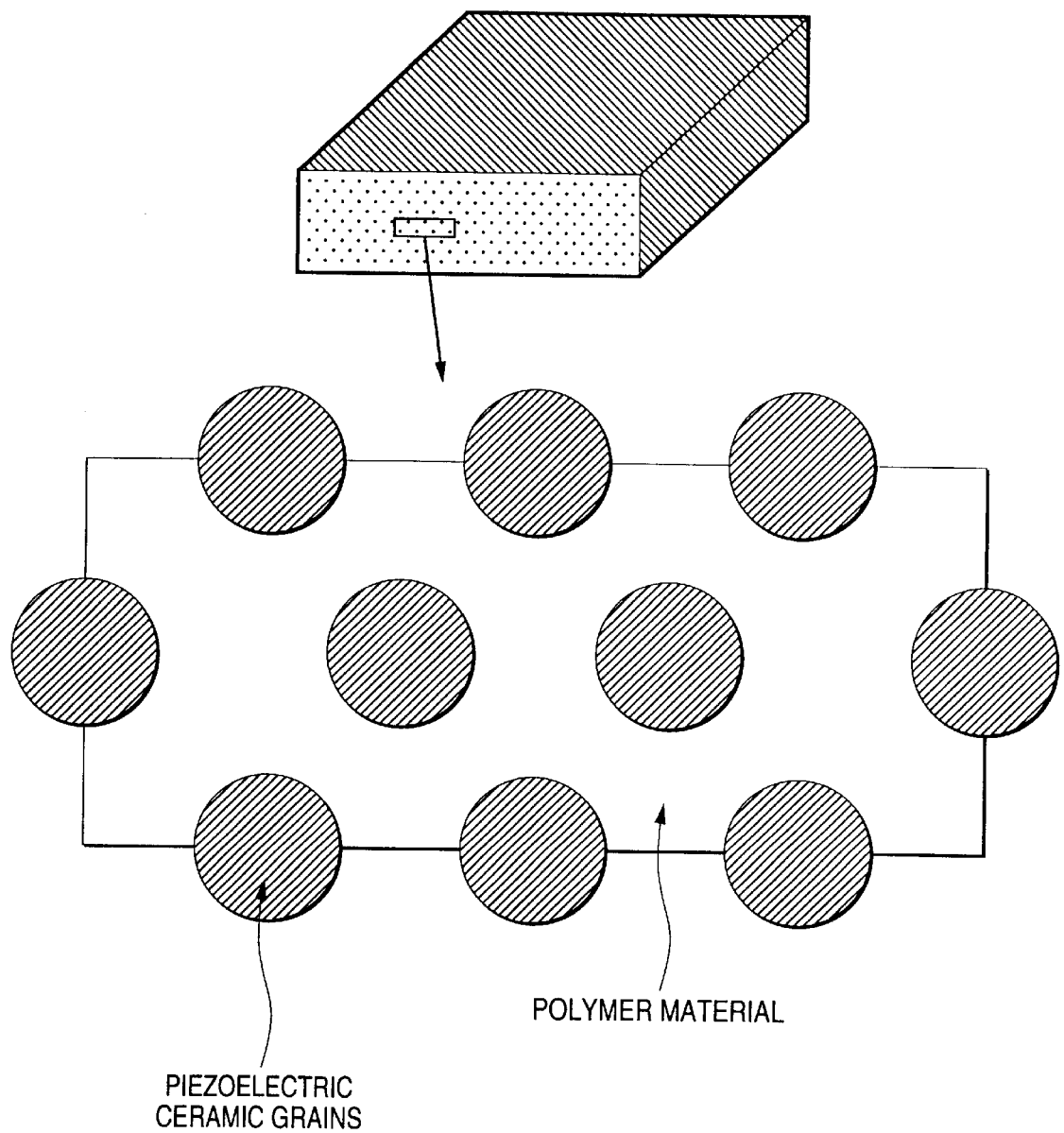
FIG. 25 shows still another example of they piezoelectric element for the invention (this is a 0-3 type piezocomposite material).

Next, four actual surface flaws for each of five roll material in Table 1, totaling 20 surface defects in all rolls, were sampled, and the S/N ratios of the reflected waves from those surface flaws were measured. FIG. 19 is a graph of the thus-measured data, in which the horizontal axis indicates the serial numbers of those 20 surface flaws, and the vertical axis indicates the signal-to-noise ratio of reflected wave from each surface flaw. In this experiment, used were the above-mentioned three probes, Probe F, Probe G and Probe H. From FIG. 19, it has been verified that Probe F of the invention can detect the actual surface flaws in a stable manner at high S/N ratios.

The invention has been described concretely hereinabove. However, the invention is not limited to only the above-mentioned embodiments but can be changed and modified in different manners without overstepping the spirit and scope thereof.

For example, the materials of the piezoelectric element 10A, the clamping block 10B and the resin wedge 10C that constitute the surface wave probe are not limited to only those shown in the above-mentioned embodiments, and any other materials having the same functions are usable herein.

In the above-mentioned embodiments, water is used as the coupling medium. Apart from this, any other liquids such as oils, etc. may be used herein.

The subjects to which the invention is applied are not limited to only rolls for rolling mills, especially to high-speed tool steel rolls, but include any columnar structures such as rollers of metals and others with no specific limitation.

TABLE 1

| Roll No. (Roll Material) | Manufacturer | Production Method | Surface Wave Velocity (m/sec.) |
|---|---|---|---|
| #1 | A Company | continuous casting with build-up surfacing | 3158 |
| #2 | A Company | centrifugal casting | 3110 |
| #3 | B Company | centrifugal casting | 3168 |
| #4 | C Company | centrifugal casting | 3090 |
| #5 | D Company | forging | 3180 |

TABLE 2 volume fraction of metallic tungsten powder: 80 %

| Piezoelectric Material | Resin Material | Frequency Bandwidth (%) | Pulse Length/Wavelength | Height of Reflected Waves from Primary Cracks (dB) | Remarks |
|---|---|---|---|---|---|
| Lead Meta-niobate | Polyimide | 75 | 1.5 | −13.5 | Examples of the Invention |
| | Polystyrol | 75 | 1.5 | −13.4 | Invention |
| | Acryl | 70 | 1.5 | −12.8 | |
| | Teflon | 70 | 1.5 | −12.5 | |
| Lead Titanate | Polyimide | 62 | 2 | −12 | |
| | Polystyrol | 63 | 2 | −12.4 | |
| | Acryl | 60 | 2 | −11.6 | |
| | Teflon | 59 | 2 | −11.8 | |
| 1-3 Type Piezocomposite | Polyimide | 75 | 1.5 | −13.2 | |
| | Polystyrol | 73 | 1.5 | −13.4 | |
| | Acryl | 70 | 1.5 | −12.4 | |
| | Teflon | 69 | 1.5 | −12.6 | |
| 0-3 Type Piezocomposite | Polyimide | 61 | 2 | −12 | |
| | Polystyrol | 61 | 2 | −11.8 | |
| | Acryl | 58 | 2 | −11.6 | |
| | Teflon | 58 | 2 | −11.8 | |

TABLE 2-continued volume fraction of metallic tungsten powder: 80 %

| Piezoelectric Material | Resin Material | Frequency Bandwidth (%) | Pulse Length/Wavelength | Height of Reflected Waves from Primary Cracks (dB) | Remarks |
|---|---|---|---|---|---|
| 3-1 Type Piezocomposite | Polyimide | 62 | 2 | −11.6 | |
| | Polystyrol | 62 | 2 | −11.4 | |
| | Acryl | 60 | 2 | −11.6 | |
| | Teflon | 59 | 2 | −11.8 | |
| PZT | Polyimide | 38 | 3.5 | −9.6 | Comparative Examples |
| | Polystyrol | 38 | 3.5 | −9.4 | |
| | Acryl | 37 | 3.5 | −9.2 | |
| | Teflon | 36 | 3.5 | −9 | |

TABLE 3 volume fraction of metallic tungsten powder: 60 %

| Piezoelectric Material | Resin Material | Frequency Bandwidth (%) | Pulse Length/Wavelength | Height of Reflected Waves from Primary Cracks (dB) | Remarks |
|---|---|---|---|---|---|
| Lead Meta-niobate | Polyimide | 62 | 2 | −12.4 | Examples of the Invention |
| | Polystyrol | 62 | 2 | −12.3 | |
| | Acryl | 60 | 2 | −12.1 | |
| | Teflon | 60 | 2 | −12.1 | |
| Lead Titanate | Polyimide | 52 | 2.5 | −11.1 | |
| | Polystyrol | 52 | 2.5 | −11 | |
| | Acryl | 50 | 2.5 | −11 | |
| | Teflon | 50 | 2.5 | −11.1 | |
| 1-3 Type Piezocomposite | Polyimide | 61 | 2 | −12.4 | |
| | Polystyrol | 60 | 2 | −12.2 | |
| | Acryl | 60 | 2 | −12 | |
| | Teflon | 60 | 2 | −12.1 | |
| 0-3 Type Piezocomposite | Polyimide | 51 | 2.5 | −11.2 | |
| | Polystyrol | 51 | 2.5 | −11.2 | |
| | Acryl | 50 | 2.5 | −11 | |
| | Teflon | 50 | 2.5 | −11 | |
| 3-1 Type Piezocomposite | Polyimide | 52 | 2.5 | −11.3 | |
| | Polystyrol | 50 | 2.5 | −11 | |
| | Acryl | 50 | 2.5 | −11 | |
| | Teflon | 50 | 2.5 | −11 | |
| PZT | Polyimide | 32 | 4 | −9 | Comparative Examples |
| | Polystyrol | 33 | 4 | −8.8 | |
| | Acryl | 31 | 4 | −8.9 | |
| | Teflon | 31 | 4 | −8.7 | |

TABLE 4 volume fraction of metallic tungsten powder: 40%

| Piezoelectric Material | Resin Material | Frequency Bandwidth (%) | Pulse Length/Wavelength | Height of Reflected Waves from Primary Cracks (dB) | Remarks |
|---|---|---|---|---|---|
| Lead Metal-niobate | Polyimide | 52 | 2.5 | −11.4 | Examples of the Invention |
| | Polystyrol | 52 | 2.5 | −11.3 | |
| | Acryl | 50 | 2.5 | −11.1 | |
| | Teflon | 50 | 2.5 | −11.1 | |
| 1-3 Type Piezocomposite | Polyimide | 51 | 2.5 | −11.1 | |
| | Polystyrol | 51 | 2.5 | −11 | |
| | Acryl | 50 | 2.5 | −11.1 | |
| | Teflon | 50 | 2.5 | −11 | |

TABLE 4-continued volume fraction of metallic tungsten powder: 40%

| Piezoelectric Material | Resin Material | Frequency Bandwidth (%) | Pulse Length/Wavelength | Height of Reflected Waves from Primary Cracks (dB) | Remarks |
|---|---|---|---|---|---|
| PZT | Polyimide | 27 | 5 | −8.4 | Comparative Examples |
| | Polystyrol | 26 | 5 | −8.6 | |
| | Acryl | 26 | 5 | −8.4 | |
| | Teflon | 26 | 5 | −8.5 | |

TABLE 5 volume fraction of metallic tungsten powder: 20%

| Piezoelectric Material | Resin Material | Frequency Bandwidth (%) | Pulse Length/Wavelength | Height of Reflected Waves from Primary Cracks (dB) | Remarks |
|---|---|---|---|---|---|
| Lead Metal-niobate | Polyimide | 52 | 2.5 | −10.6 | Comparative Examples |
| | Polystyrol | 52 | 2.5 | −10.4 | |
| | Acryl | 50 | 2.5 | −10.3 | |
| | Teflon | 50 | 2.5 | −10.4 | |
| 1-3 Type Piezocomposite | Polyimide | 51 | 2.5 | −10.5 | |
| | Polystyrol | 51 | 2.5 | −10.4 | |
| | Acryl | 50 | 2.5 | −10.3 | |
| | Teflon | 50 | 2.5 | −10.2 | |
| PZT | Polyimide | 22 | 6 | −8.2 | |
| | Polystyrol | 21 | 6 | −8 | |
| | Acryl | 20 | 6 | −8.1 | |
| | Teflon | 20 | 6 | −8.1 | |

INDUSTRIAL APPLICABILITY

According to the present invention for surface wave testing, false detection of primary cracks is prevented and overgrinding that causes the increase in the roll consumption is prevented. In addition, the level of structual noises from primary cracks and grain boundaries is lowered, and the detectability of the apparatus are greatly enhanced.

In particular, in the process on the basis of the invention where rolls having been thermally/mechanically damaged in their surfaces while they are used in rolling are ground and the grinding allowance of each roll is settled according to the height of the reflected waves from the thermally/mechanically damaged parts, the decrement in diameter of each roll by grinding is optimized to reduce the roll consumption and to improve the roll grinding efficiency.

In applications of surface wave testing of rolls on the basis of the invention, the surface wave probe can produce and receive the surface wave at high efficiency, irrespective of the difference in roll materials as produced in different methods. In those, therefore, one and the same surface wave probe is usable in testing of rolls of different materials without exchanging it, and the surface wave probe common to such different rolls ensures increased signal-to-noise ratios for the reflected waves from flaws.

What is claimed is:

1. A method for ultrasonic testing of columnar structures, wherein a surface wave probe is contacted with the surface of a rotating columnar structure via a coupling medium existing therebetween, and surface waves are propagated into the columnar structure from said surface wave probe while the probe receives reflected waves from corresponding flaws existing in and just below the surface of the columnar structure so as to detect said flaws;

the method being characterized in that, a center frequency of the surface waves to be transmitted and received by said surface wave probe is in a frequency spectrum of said surface waves, and a frequency bandwidth within which a peak value and a peak value−6 dB covers at least 0.50 fc or larger.

2. A method for ultrasonic testing of columnar structures, wherein a surface wave probe is contacted with the surface of a rotating columnar structure via a coupling medium existing therebetween, and surface waves are propagated into the columnar structure from said surface wave probe while the probe receives reflected waves from corresponding flaws existing in and just below the surface of the columnar structure so as to detect said flaws;

the method being characterized in that the pulse duration of the surface wave pulse which said surface wave probe transmits and receives is at most 2.5 times the period of the surface waves that propagate into said columnar structure.

3. An apparatus for ultrasonic testing of columnar structures, wherein a surface wave probe is contacted with the surface of a rotating columnar structure via a coupling medium existing therebetween, and surface waves are propagated into the columnar structure from said surface wave probe while the probe receives reflected waves from corresponding flaws existing in and just below the surface of the columnar structure so as to detect said flaws;

the apparatus is characterized in that said surface wave probe that transmits and receives said surface waves is provided with a wedge as disposed on a front surface of a piezoelectric element of the probe and with a damping block disposed on a back surface of the piezoelectric element, wherein the pulse length of the surface wave pulse which the surface wave probe transmits and receives is at most 2.5 times the wavelength of the surface waves that propagate into the columnar structure.

4. The apparatus for ultrasonic testing of columnar structures as claimed in claim 3, wherein said piezoelectric element is any of a lead meta-niobate, a lead titanate, a 1-3 type piezocomposite material, a 0-3 type piezocomposite material, or a 3-1 type piezocomposite material.

5. The apparatus for ultrasonic testing of columnar structures as claimed in claim 3, wherein said wedge has an attenuation coefficient (for longitudinal waves) at 2 MHz of not larger than $1.8 \times 10^2$ dB/m.

6. The apparatus for ultrasonic testing of columnar structures as claimed in claim 5, wherein said wedge is made of a polyimide resin, a polystyrol resin, an acrylic resin, or a fluorine resin.

7. The apparatus for ultrasonic testing of columnar structures as claimed in claim 3, wherein said damping block has a volume fraction of metallic tungsten powder of at least 40% or larger.

8. The apparatus for ultrasonic testing of columnar structures as claimed in claim 3, wherein said wedge has a bottom surface at which it is contacted with the surface of the columnar structure via a coupling liquid medium existing therebetween, and has an inclined surface of such that its normal line intersects the normal line of said bottom surface at an incident angle θi to be defined by the following formula:

$$\theta i = \sin^{-1}(Cw/Cr)$$

where Cw indicates the velocity of the ultrasonic wave in the wedge, and

Cr indicates the velocity of the surface wave traveling in the columnar structure, and wherein the front surface of said piezoelectric element is attached to said inclined surface of the wedge.

9. The apparatus for ultrasonic testing of columnar structures as claimed in any claim 3, wherein said columnar structure is a high-speed tool steel roll.

10. The apparatus for ultrasonic testing of columnar structures as claimed in claim 8, wherein the velocity of the surface waves traveling in the columnar structure, Cr in the formula that defines the incident angle θi is a mean value, CRav, of the velocity of the surface wave traveling in each roll to be tested.

11. An apparatus for ultrasonic testing of columnar structures, wherein a surface wave probe is contacted with the surface of a rotating columnar structure via a coupling liquid medium existing therebetween, and a surface wave is propagated into the columnar structure from said surface wave probe while the probe receives reflected waves from corresponding flaws existing in and just below the surface of the columnar structure so as to detect said flaws, the apparatus comprising:

columnar structure-rotating means for rotating said columnar structure in the circumferential direction of the structure, rotating speed-monitoring means for monitoring the rotating speed of the columnar structure being rotated by said columnar structure-rotating means, holder means for holding said surface wave probe above the columnar structure to ensure a predetermined distance between the probe and the surface of the columnar structure, scanning means for scanning said holding means in the axial direction of the columnar structure, couplant supply means capable of supplying a liquid medium to be a coupling medium for ultrasonic waves to the gap between said surface wave probe and a surface of the columnar structure and provided with a flow control valve capable of controlling the flow rate of the liquid medium in accordance with the rotating speed of the columnar structure to be rotated by said columnar structure-rotating means, a surface wave probe which is provided with a piezoelectric element, a wedge disposed on the front surface of a piezoelectric element and a damping block disposed on the back surface of the piezoelectric element, so that, where the center frequency of the surface wave to be transmitted and received by said surface wave probe is fc in the frequency spectrum of the surface waves, a frequency bandwidth within which a spectrum magnitude falls in the range between the peak value and the peak value−6 dB covers at least 0.50 fc or larger, and that the surface wave probe is capable of detecting the flaws in the columnar structure by use of surface waves, an ultrasonic pulser/receiver capable of supplying said surface wave probe with an electric pulse for producing surface waves and capable of amplifying the signals which said surface wave probe has received to a level necessary for flaw detection and outputting them, gating means for extracting the signals for flaw detection from the signals which said ultrasonic pulser/receiver has outputted, and outputting them, and peak detector/comparator means for detecting the amplitude of the signals which the gating means has outputted, and outputting the thus-detected signals, or for comparing the amplitude of the signals which the gating means has outputted with a predetermined threshold voltage and, when the amplitude of the signals from the gating means are larger than the predetermined threshold voltage, outputting signals that indicate the presence of flaws in the columnar structure being tested.

* * * * *